United States Patent
Pritelli et al.

(10) Patent No.: US 10,175,288 B2
(45) Date of Patent: Jan. 8, 2019

(54) ELECTRONIC DEVICE, SYSTEM AND METHOD FOR INSULATION RESISTANCE MEASUREMENTS WITH FUNCTIONS OF SELF-DIAGNOSIS AND DIAGNOSIS OF INSULATION LOSS WITH RESPECT TO GROUND OF AN ENERGIZED ELECTRICAL APPARATUS

(71) Applicant: MAGNETI MARELLI S.P.A., Corbetta (IT)

(72) Inventors: Danilo Pritelli, Bologna (IT); Rosanna Suglia, Bologna (IT); Gianluca Aurilio, Capua (IT); Alessandro Cerutti, Bologna (IT); Franco Ciampolini, Bologna (IT)

(73) Assignee: MAGNETI MARELLI S.p.A., Corbetta (IT)

( * ) Notice: Subject to any disclaimer, the term of this patent is extended or adjusted under 35 U.S.C. 154(b) by 57 days.

(21) Appl. No.: 15/378,922

(22) Filed: Dec. 14, 2016

(65) Prior Publication Data

US 2017/0176512 A1 Jun. 22, 2017

(30) Foreign Application Priority Data

Dec. 18, 2015 (IT) .................. 102015000084957

(51) Int. Cl.
*H01H 31/12* (2006.01)
*G01R 31/12* (2006.01)
(Continued)

(52) U.S. Cl.
CPC ....... *G01R 31/12* (2013.01); *G01R 19/16566* (2013.01); *G01R 31/006* (2013.01);
(Continued)

(58) Field of Classification Search
CPC ... H01G 2/00; G01R 1/00; G01N 1/00; G01N 2201/00
See application file for complete search history.

(56) References Cited

U.S. PATENT DOCUMENTS

2002/0130668 A1* 9/2002 Blades .................. G01R 1/07
324/536
2004/0189330 A1* 9/2004 Herb .................... G01R 27/18
324/691
(Continued)

FOREIGN PATENT DOCUMENTS

DE 3346387 A1 7/1985
DE 102010006108 A1 8/2011

OTHER PUBLICATIONS

Search Report and Written Opinion issued by the Italian Patent Office for Italian Application No. IT UB20159266 dated Sep. 2, 2016.

*Primary Examiner* — Jermele M Hollington
*Assistant Examiner* — Temilade Rhodes-Vivour
(74) *Attorney, Agent, or Firm* — Howard & Howard Attorneys PLLC

(57) ABSTRACT

An electronic device for the diagnosis of insulation loss of an energized electrical apparatus, with respect to a ground. The device includes a first resistance-switch group and a second resistance-switch group, connectable or disconnectable in a controlled manner, and also a first measurement circuit and a second measurement circuit, arranged in parallel to the first and second resistance-switch groups, respectively. The first and second measurement circuits include respective first and second detection circuits, first and second charge modulation circuits and first and second partition resistors ($RB_{minus}$, $RB_{plus}$). The first and second charge modulation circuits allow a dynamic "switching" measurement technique. Moreover, a method is described for mea- (Continued)

suring the insulation resistances ($RI_{minus}$, $RI_{plus}$) of an energized electrical apparatus with respect to ground, in which the method is carried out by a device according to the invention. Finally, a self-diagnosis method of device is described.

24 Claims, 6 Drawing Sheets

(51) Int. Cl.
*G01R 19/165* (2006.01)
*G01R 31/00* (2006.01)
*G07C 5/08* (2006.01)
*H01G 2/00* (2006.01)
*G01N 1/00* (2006.01)

(52) U.S. Cl.
CPC ........... *G01N 1/00* (2013.01); *G01N 2201/00* (2013.01); *G07C 5/0808* (2013.01); *H01G 2/00* (2013.01)

(56) References Cited

U.S. PATENT DOCUMENTS

| | | | |
|---|---|---|---|
| 2005/0225909 A1* | 10/2005 | Yoshizaki | H01H 83/144 361/42 |
| 2009/0001993 A1 | 1/2009 | Lindsey et al. | |
| 2010/0063660 A1 | 3/2010 | Uchida | |
| 2010/0308841 A1* | 12/2010 | Karrer | G01R 27/025 324/551 |
| 2010/0315096 A1 | 12/2010 | Yamamoto et al. | |
| 2011/0084705 A1* | 4/2011 | Kawamura | G01R 27/025 324/551 |
| 2011/0140714 A1* | 6/2011 | Hernando | G01R 27/025 324/551 |
| 2014/0159908 A1 | 6/2014 | Hong et al. | |

* cited by examiner

ELECTRONIC DEVICE, SYSTEM AND METHOD FOR INSULATION RESISTANCE MEASUREMENTS WITH FUNCTIONS OF SELF-DIAGNOSIS AND DIAGNOSIS OF INSULATION LOSS WITH RESPECT TO GROUND OF AN ENERGIZED ELECTRICAL APPARATUS

CROSS-REFERENCE TO RELATED APPLICATIONS

The present application claims priority to and all the benefits of Italian Patent Application No. 102015000084957, filed on Dec. 18, 2015, both of which are hereby expressly incorporated herein by reference in their entirety.

BACKGROUND OF THE INVENTION

1. Field of the Invention

The present invention relates to a device, a system and a method for measuring the insulation resistance of an energized electrical apparatus with respect to ground, and therefore also for a diagnosis of insulation loss of such an apparatus.

It is worth noting that, although the present description particularly illustrates the application of the invention to a battery for an electric or hybrid motor by way of example, it will be apparent that the invention is in the same manner applicable to any energized electrical apparatus or system with respect to earth or to a generic reference or safety ground.

The present invention also relates to a self-diagnosis method of the above device.

2. Description of the Related Art

The ever-increasing diffusion in the use of electrochemical batteries with high nominal voltages, for example in electric and hybrid vehicles, results in the possibility of electrical risk associated with the use of such voltages which are potentially dangerous for persons and things. Therefore, the danger associated with the use of electricity, to date considered mainly associated with the use of electricity within working or domestic context, now arises also on electric or hybrid vehicles equipped with storage systems characterized by potentially dangerous electric voltages.

The further diffusion of electrical traction on vehicles, expected in the next few years, associated with the frequent and widespread use thereof for transporting persons and things, could result in the electrical risk and potential danger associated with the use of lithium batteries for traction becoming in the future one of the main causes of risk for the safety of persons using such means of transportation.

Possible drawbacks (such as for example, malfunctioning due to the obsolescence of the components of the electrical apparatus, dielectric breakdown or electric discharges) pose the problem of protection from potentially dangerous events, such as the occurrence of short-circuits or insulation losses, which may cause fires and/or explosions, which may be also particularly serious if they are in the presence of flammable or explosive substances, and such as to even put people's lives in danger.

Among such possible drawbacks, insulation loss of the battery voltage with respect to the earth or to a generic reference or safety ground (such as for example, the chassis of the vehicle) is one of the faults which may occur most frequently.

For example, in the case of a fault due to a cable with a damaged sheath in contact with the vehicle body, a drastic decrease of the insulation resistance is generated between the high-voltage circuit and the vehicle body. Such a decrease in the insulation resistance can be diagnosed by means of an electronic circuit, also of known type, which is capable of detecting the insulation resistance.

Indeed, the use is known in electric and hybrid vehicles equipped with high-voltage systems, of am insulation detection circuit, which is conveniently inserted in the electrical system and is capable of measuring in "run-time" the insulation resistance between the high-voltage circuit and the chassis of the vehicle.

The specific safety and person protection requirements against electrical risks which are applicable to rechargeable energy storage systems on board electric vehicles (both battery-operated electric vehicles and vehicles with "fuel-cells") and hybrid vehicles are defined in international Standard ISO 6469. Further safety related aspects refer to Standard ISO 26262.

Among the various safety and protection requirements, in ISO 6469, inter alia, the possibility is indicated of using a system for monitoring the insulation resistance by means of an "insulation resistance monitoring system" installed on the vehicle to check the integrity of the high-voltage circuit of the battery by means of a periodic measurement (preferably performed automatically) of the value of the insulation resistance of the battery with respect to earth or to a generic reference or safety ground.

However, the desired functionality of automatically performing the insulation resistance measurement poses the significant technical problem of succeeding in discriminating whether, with respect to an anomalous measurement of the insulation resistance, this is due to a fault of insulation loss of the battery with respect to the ground or to a fault of the insulation resistance measurement circuit itself.

Moreover, the further and even more critical technical problem arises of remediating possible circumstances in which the insulation resistance measurement circuit has failed, or was damaged, or has deteriorated over time, and accordingly is no longer capable of recognizing an insulation loss if this occurs.

With respect to the above, the need is strongly felt for the insulation resistance measurement circuit or system to have effective self-diagnosis functionalities adapted to avoid that a fault in the circuit may compromise the correct detection of the insulation loss.

Additionally, there is an ever-increasing need for accuracy in the measurement of insulation resistance in order to provide accurate information to the battery management system and to render the subsequent safety and protection procedures more timely and effective.

Within the background herein considered, the solutions for the insulation resistance measurement that are currently known and employed do not fully meet the above-illustrated needs and requirements.

Indeed, although the prior art has several solutions for making circuits adapted to measure the insulation resistance of an apparatus with respect to a generic ground or chassis, such known solutions do not resolve, and often do not even consider the issue of the electronic circuit adapted to insulation resistance measurement having a good or increased "diagnosability". Such an aspect, although underestimated, is very delicate because, as noted above, a breakdown or alteration of the insulation resistance measurement circuit, which in practice is rather frequent, may result in an incorrect detection of fault circumstances that nay be potentially dangerous for the health of people.

In light of the above, the need is strongly felt, mainly within the scope of automobile applications but also within other application scopes (it is easy to understand that similar needs may emerge for energized apparatuses other than a battery and used in other contexts), to provide an electronic measurement device of the insulation resistance that is conveniently designed both to perform the primary task of accurately measuring the value of the insulation resistance and to allow self-diagnosis procedures in order to avoid possible circumstances failed or incorrect detection of insulation loss.

SUMMARY OF THE INVENTION

It is the object of the present invention to provide an electronic device for insulation resistance measurement, and therefore for a diagnosis of insulation loss, such as to allow at least partly obviating the drawbacks indicated above with reference to the known art and to allow meeting the above-mentioned needs, particularly felt in the technical field considered.

In particular, the device for measuring the insulation resistance of the present invention provides a solution both to the problem of the accurate measurement of the insulation resistance and to the problem of the self-diagnosis of the device itself, without resorting to costly redundant measurement circuits.

To this end, the device of the invention provides a "dynamic" type measurement (and not a "static" type measurement, as in known solutions) based on a particular switching technique capable of detecting deterioration or breakdown problems of the device itself in a more effective manner.

It is also the object of the invention to provide a system and a method for measuring insulation resistance and for a diagnosis of insulation loss employing the aforesaid device.

Closely correlated with the above-mentioned objects, there is the further object of providing a method for the self-diagnosis of the aforesaid device, that is a method adapted to check the correct functionality, or lack thereof, of the device and to identify possible faults.

The aforesaid device, system, measurement method and self-diagnosis method may be mainly employed within the "automotive" scope, for example in motion systems for an electric traction or hybrid vehicle with a class B battery (from 60 V DC to 1500 V DC).

However, they may be used profitably in all other contexts or applications requiring a continuous monitoring of the insulation resistance of a circuit with respect to a generic ground or safety system.

The above-mentioned objects are achieved by an electronic device for the diagnosis of insulation loss, with respect to a ground of an energized electrical apparatus having a negative terminal and a positive terminal, through the measurement of a negative terminal insulation resistance ($RI_{minus}$) present between the negative terminal and the round and a positive terminal insulation resistance $RI_{plus}$ present between the positive terminal and the ground. The device includes a first device terminal and a second device terminal, suitable to be connected, respectively, to the negative and positive terminals of the energized electrical apparatus. A first resistance-switch group includes a first sample resistance ($RS_{minus}$) adapted to be connected or disconnected in a controlled manner between the first device terminal and the ground by a first sample resistance insertion switch ($S_{minus}$). A first measurement circuit is arranged between the first device terminal and the ground, in parallel to the first resistance-switch group. A second resistance-switch group includes a second sample resistance ($RS_{plus}$) adapted to be connected or disconnected in a controlled manner between the second device terminal and the ground by a second sample resistance insertion switch ($S_{plus}$). A second measurement circuit is arranged between the second device terminal and the ground, in parallel to the second resistance-switch group. The first measurement circuit includes a first detection circuit, comprising at least a first resistor (R2) and a first capacitor (C1) arranged mutually in parallel, so that at the ends of the first capacitor (C1), after the first device terminal is connected to the energized electrical apparatus and reaches a first steady state, there is a first detection voltage ($VC_{minus}$) depending on the negative voltage ($V_{minus}$) of the energized electrical apparatus. The first detection circuit further includes a first voltage meter ($U_{minus}$); a first charge modulation circuit arranged in parallel to the first detection circuit and comprising a first modulation resistance (R1) and a first modulation switch (SW1), arranged in series with the first modulation resistance (R1) and adapted to be controlled by a first driving signal ($V_{SW-minus}$). When the first device terminal is connected to the energized electrical apparatus, the first capacitor (C1) is partially discharged and recharged, respectively, during each closing and opening period of the first modulation switch (SW1), so that the first detection voltage ($VC_{minus}$) oscillates between a first detection voltage maximum value ($VC_{minus-MAX}$) and a first detection voltage minimum value ($VC_{minus-MIN}$), around a first detection voltage intermediate value ($VC_{minus}$) representative of the negative voltage ($V_{minus}$) of the energized electrical apparatus. A first partition resistor ($RB_{minus}$) is connected between the first device terminal and the first detection circuit so that the first partition resistor ($RB_{minus}$) and the first detection circuit are arranged mutually in series. The second measurement circuit includes a second detection circuit, comprising at least a second resistor (R6) and a second capacitor (C2) arranged mutually in parallel, so that at the ends of the second capacitor (C2), after the second device terminal is connected to the energized electrical apparatus and reach a second steady state, there is a second detection voltage ($VC_{plus}$) depending on the positive voltage ($V_{plus}$) of the energized electrical apparatus. The second detection circuit further includes a second voltage meter ($U_{plus}$); a second charge modulation circuit, arranged in parallel to the second detection circuit, and comprising a second modulation resistance (R5) and a second modulation switch (SW2), arranged in series with the second modulation resistance (R5) and adapted to be controlled by a second driving signal ($V_{plus-MAX}$). When the second device terminal is connected to the energized electrical apparatus, the second capacitor (C2) is partially discharged and recharged, respectively, during each closing and opening period of the second modulation switch (SW2), so that the second detection voltage ($VC_{plus}$) oscillates between a second detection voltage maximum value ($VC_{plus-MAX}$) and a second detection voltage minimum value ($VC_{plus-MIN}$), around a second detection voltage intermediate value ($VC_{plus}$) representative of the positive voltage ($V_{plus}$) of the energized electrical apparatus. A second partition resistor ($RB_{plus}$) is connected between the second device terminal and the second detection circuit so that the second partition resistor ($RB_{plus}$) and the second detection circuit are arranged mutually in series. The first voltage meter ($U_{minus}$) provides the first detection voltage ($VC_{minus}$) under both opening and closing conditions of the first resistance-switch group switch ($S_{minus}$), in which conditions the first sample resistance ($RS_{minus}$) is connected and disconnected, respectively. The second voltage meter ($U_{plus}$) provides the second detection voltage ($VC_{plus}$) under both opening and closing conditions of the second resistance-switch group switch ($S_{plus}$), in which conditions the second sample resistance ($RS_{plus}$) is connected and disconnected, respectively.

The present invention is also directed toward a system according to the invention employing the aforesaid device.

In addition, the present invention is directed toward a method for measuring a negative terminal insulation resistance ($RI_{minus}$), present between a negative terminal and the ground of an energized electrical apparatus and a positive terminal insulation resistance ($RI_{plus}$), present between a positive terminal and the ground of the energized electrical apparatus. The method comprises the steps of:

connecting a first measurement circuit between the negative terminal and ground to detect a first value ($VC1_{minus}$) of a first detection voltage ($VC_{minus}$), depending on the negative voltage ($V_{minus}$) of the energized electrical apparatus;

connecting a second measurement circuit between the positive terminal and ground to detect a first value ($VC1_{plus}$) of a second detection voltage ($VC_{plus}$), depending on the positive voltage ($V_{plus}$) of the energized electrical apparatus;

alternatively, connecting a first sample resistance ($RS_{minus}$) in parallel to the first measurement circuit between the negative terminal and ground, or connecting a second sample resistance ($RS_{plus}$) in parallel to the second measurement circuit between the positive terminal and ground; under the connection condition of connection of one of the first sample resistance ($RS_{minus}$) and the second sample resistance ($RS_{plus}$), detecting a second value ($VC2_{minus}$) of the first detection voltage ($VC_{minus}$), and detecting a second value ($VC2_{plus}$) of the second detection voltage ($VC_{plus}$); and calculating the negative terminal insulation resistance ($RI_{minus}$) and the positive terminal insulation resistance ($RI_{plus}$) of the energized electrical apparatus, on the basis of the first value of first detection voltage ($VC1_{minus}$), second value of first detection voltage ($VC2_{minus}$), first value of second detection voltage ($VC1_{plus}$) and second value of second detection voltage ($VC2_{plus}$).

The step of detecting a first value of first detection voltage ($VC1_{minus}$) includes modulating the first detection voltage ($VC_{minus}$) by use of a modulation signal, detecting the modulated first detection voltage ($VC_{minus}$), and determining the first value of first detection voltage ($VC1_{minus}$) on the basis of the modulated first detection voltage ($VC_{minus}$). The step of detecting a first value of second detection voltage ($VC1_{plus}$) includes modulating the second detection voltage ($VC_{plus}$) by of a modulation signal, detecting the modulated second detection voltage ($VC_{plus}$), and determining the first value of second detection voltage ($VC1_{plus}$) on the basis of the modulated second detection voltage ($VC_{plus}$). The step of detecting a second value of first detection voltage ($VC2_{minus}$) includes modulating again the first detection voltage ($VC_{minus}$) by of the modulation signal, while the first sample resistance ($RS_{minus}$) or second sample resistance ($RS_{plus}$) is connected; detecting again the modulated first detection voltage ($VC_{minus}$); determining the second value of first detection voltage ($VC2_{minus}$) on the basis of the modulated first detection voltage ($VC_{minus}$), detected while said first sample resistance ($RS_{minus}$) or second sample resistance ($RS_{plus}$) is connected. The step of detecting a second value of second detection voltage ($VC2_{plus}$) includes modulating again the second detection voltage ($VC_{plus}$) by of the modulation signal, while the first sample resistance ($RS_{minus}$) or second sample resistance ($RS_{plus}$) is connected; detecting again the modulated second detection voltage ($VC_{plus}$); determining the second value of second detection voltage ($VC2_{plus}$) on the basis of the modulated second detection voltage ($VC_{plus}$), while the first sample resistance ($RS_{minus}$) or second sample resistance ($RS_{plus}$) is connected.

The present invention is also directed toward a method of self-diagnosis of an electronic device for diagnosing the insulation loss of an energized electrical apparatus.

Other objects, features and advantages of the present invention will be readily appreciated as the same becomes better understood after reading the subsequent description taken in connection with the accompanying drawings.

BRIEF DESCRIPTION OF THE DRAWINGS

Further features and advantages of such an electronic device and system according to the invention will become apparent from the following description of preferred embodiments thereof, given only by way of non-limiting, indicative example, with reference to the accompanying drawings, in which.

It is worth noting that equal or similar elements in the aforesaid drawings are indicated with the same numbers and/or letters.

DETAILED DESCRIPTION

Figure 1:
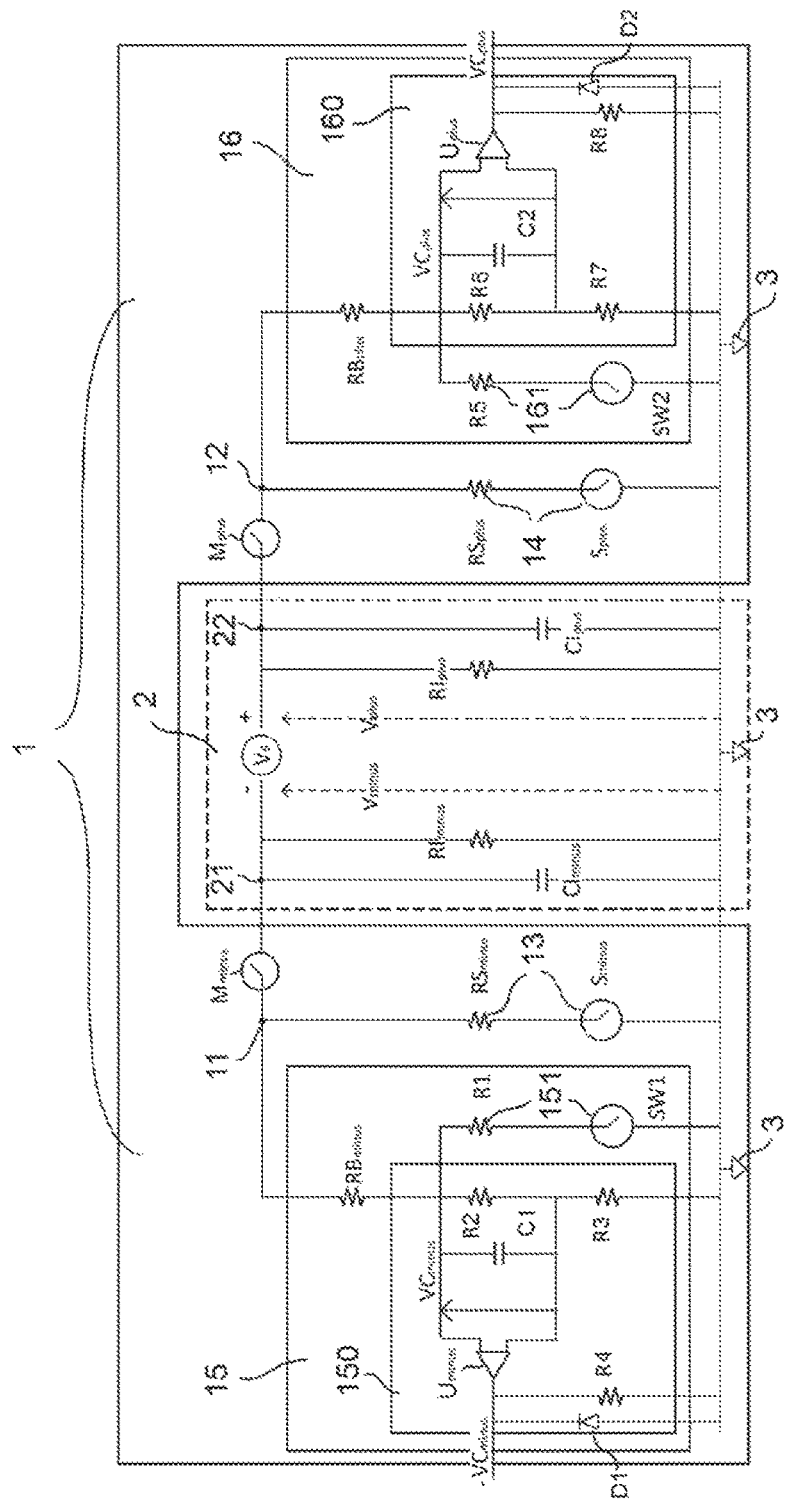
FIG. 1 shows a schematic diagram of an electronic device according to one embodiment of the present invention, in association with a battery of which the insulation resistance has to be measured.

With reference to FIG. 1, firstly there is described an electronic device 1 for the diagnosis of the insulation loss, with respect to a ground 3, of an energized electrical apparatus 2 having a negative terminal 21 and a positive terminal 22, through the measurement of the insulation resistance $RI_{minus}$ referring to the negative terminal 21, that is present between the negative terminal 21 and ground 3 of apparatus 2, and of the insulation resistance $RI_{plus}$ referring to the positive terminal 22, that is present between the positive terminal 22 and ground 3 of apparatus 2.

It is worth noting that the aforesaid insulation resistances $RI_{minus}$ and $RI_{plus}$ are parasitic resistances: indeed, under ideal conditions, the insulation resistances between terminals of the energized electrical apparatus 2 and ground 3 should be virtually infinite value resistances.

It is also worth noting that the energized electrical apparatus 2 with which the device is associated, is, in a preferred application example, a battery 2 for electric or hybrid motor, in the automotive field. However, in other examples of the application of device 1, such an apparatus may be any other system (such as for example, an inverter, again in the automotive field, or an electric apparatus used in any other field) which is energized with respect to earth or to a generic reference or safety ground.

Device 1 comprises a first device terminal 11 and a second device terminal 12, adapted to be connected to the negative 21 and positive 22 terminals, respectively, of the energized electrical apparatus 2. Moreover, device 1 comprises a first resistance-switch group 13, a second resistance-switch group 14, a first measurement circuit 15, arranged between the first device terminal 11 and the ground 3 in parallel to the first resistance-switch group 13, and a second measurement circuit 16, arranged between the second device terminal 12 and the ground 3 in parallel to the second resistance-switch group 14.

The first resistance-switch group 13 comprises a first sample resistance $RS_{minus}$ adapted to be connected or disconnected in a controlled manner between the first device terminal 11 and the ground 3 by a first sample resistance input switch $S_{minus}$.

The second resistance-switch group 14 comprises a second sample resistance $RS_{plus}$ adapted to be connected or disconnected in a controlled manner between the second device terminal 12 and the ground 3 by a second sample resistance input switch $S_{plus}$.

The first measurement circuit 15 in turn comprises a first detection circuit 150, a first charge modulation circuit 151 and a first partition resistor $RB_{minus}$ connected between the first device terminal 11 and the first detection circuit 150, so that the first partition resistor $RB_{minus}$ and the first detection circuit 150 are arranged mutually in series.

The first detection circuit 150 comprises at least a first resistor R2 and a first capacitor C1 arranged mutually in parallel, so that at the ends of the first capacitor C1, when the first device terminal 11 is connected to the energized electrical apparatus 2, after a transient required for the measurement to reach a first steady state, there is a first detection voltage $VC_{minus}$ depending on the negative voltage $V_{minus}$ of the energized electrical apparatus 2. The first detection circuit 150 further comprises a first voltage meter $U_{minus}$.

The first charge modulation circuit 151 is arranged in parallel to the first detection circuit 150 and comprises a first modulation resistance R1 and a first modulation switch SW1, which is arranged in series with the first modulation resistance R1 and is adapted to be controlled by a first driving signal $V_{SW-minus}$, so that when the first device terminal 11 is connected to the energized electrical apparatus 2, the first capacitor C1 is partially discharged and recharged during each closing and opening period of the first modulation switch SW1, respectively, so that the first detection voltage $VC_{minus}$ oscillates between a first detection voltage maximum value $VC_{minus-MAX}$ and a first detection voltage minimum value $VC_{minus-MIN}$, around a first detection voltage intermediate value $VC_{minus}$ representative of the negative voltage $V_{minus}$ of the energized electrical apparatus 2.

The second measurement circuit 16 in turn comprises a second detection circuit 160, a second charge modulation circuit 161 and a second partition resistor $RB_{plus}$ connected between the second device terminal 12 and the second detection circuit 160 so that the second partition resistor $RB_{plus}$ and the second detection circuit 160 are arranged mutually in series.

The second detection circuit 160 comprises at least a second resistor R6 and a second capacitor C2 arranged mutually in parallel, so that at the ends of the second capacitor C2, when the second device terminal 12 is connected to the energized electrical apparatus 2, after a transient required for the measurement to reach a second steady state, there is a second detection voltage $VC_{plus}$ depending on the positive voltage $V_{plus}$ of the energized electrical apparatus. The second detection circuit 160 further comprises a second voltage meter $U_{plus}$.

The second charge modulation circuit 161 is arranged in parallel to the second detection circuit 160 and comprises a second modulation resistance R5 and a second modulation switch SW2, which is arranged in series with the second modulation resistance R5 and is adapted to be controlled by a second driving signal $V_{SW-plus}$, so that, when the second device terminal 12 is connected to the energized electrical apparatus 2, the second capacitor C2 is partially discharged and recharged during each closing and opening period of the second modulation switch SW2, respectively, so that the second detection voltage $VC_{plus}$ oscillates between a second detection voltage maximum value $VC_{plus-MAX}$ and a second detection voltage minimum value $VC_{plus-MIN}$, around a second detection voltage intermediate value $VC_{plus}$ representative of the positive voltage $V_{plus}$ of the energized electrical apparatus 2.

The aforesaid first voltage meter $U_{minus}$ provides the first detection voltage $VC_{minus}$ under both opening and closing conditions of the first resistance-switch group switch $S_{minus}$, in which conditions the first sample resistance $RS_{minus}$ is connected and disconnected, respectively.

The aforesaid second voltage meter $U_{plus}$ provides the second detection voltage $VC_{plus}$ under both opening and closing conditions of the second resistance-switch group switch $S_{plus}$, in which conditions the second sample resistance $RS_{plus}$ is connected and disconnected, respectively.

According to one embodiment, the device further comprises a first device switch $M_{minus}$ adapted to connect or disconnect in a controlled manner the first terminal of device 11 to/from the negative terminal 21 of the energized electrical apparatus 2, and a second device switch $M_{plus}$ adapted to connect or disconnect in a controlled manner the second terminal of device 12 to/from the positive terminal 22 of the energized electrical apparatus 2.

In one implementing example, each of the aforesaid first device switch $M_{minus}$ and second device switch $M_{plus}$ comprises an electromechanical switch. Each of the aforesaid first modulation switch SW1 and second modulation switch SW2 comprises a respective solid state electronic switch.

According to an implementation option of the device, the first detection circuit 150 further comprises a third resistor R3 connected between the parallel of the first resistor R2 and of the first capacitor C1 and the ground 3; and the second detection circuit 160 further comprises a fourth resistor R7 connected between the parallel of the second resistor R6 and the second capacitor C2 and the ground 3.

According to an implementation example, the first detection circuit 150 further comprises an output resistor R4 and an output diode D1, which are connected between the output of the first voltage meter $U_{minus}$ and ground. Similarly, the second detection circuit 180 further comprises an output resistor R8 and an output diode D2, which are connected between the output of the first voltage meter $U_{plus}$ and ground.

According to a particular implementing example, the first measurement circuit 15 and the second measurement circuit 16 have an identical circuit structure and have electrical parameters of corresponding resistors and capacitors respectively identical.

In one implementing option, each of the aforesaid first voltage meter $U_{minus}$ and second voltage meter $U_{plus}$ comprises a respective operational amplifier.

According to an implementation example, the aforesaid first sample resistance $RS_{minus}$ and second sample resistance $RS_{plus}$ have values which conform with the ones set forth in Standard ISO 6469.

With reference to the details shown in FIG. 1 and to the conventions used, it is worth noting the following.

FIG. 1 depicts (in the dashed box) the equivalent circuit of the battery pack 2 (which is not part of the device, but in this example is the energized electrical apparatus 2 to which device 1 can be connected to perform its functions). Shown at the sides of the battery pack, and connectable to it, is the measurement device 1 of the insulation resistance of the battery pack, which consists of two parts, which are depicted in FIG. 1 to the right and to the left, respectively, of the battery pack. The two driven switches $M_{minus}$ and $M_{plus}$ can connect device 1 to the two terminals of the DC BUS when there it is required to perform the measurement of the insulation resistance, or otherwise disconnect it.

With reference to the equivalent scheme of the battery pack 2, $V_B$ indicates the voltage present between the terminals of the battery connected to the DC BUS and of which the insulation resistance with respect to a ground 3 is to be determined. Such a ground may be a safety ground, for example the chassis of the vehicle in the case of an electric vehicle, or a generic earth.

References $V_{plus}$ and $V_{minus}$ indicate, respectively, the voltage of the positive pole and the negative pole of the battery with respect to the aforesaid ground.

The relation between the aforesaid quantities $V_B = V_{plus} - V_{minus}$ is valid, where by convention, consistently to what is shown, $V_{minus}$ always has a negative sign.

The insulation resistance of the battery pack is represented by two concentrated parameters, which are not known in advance, one, indicated as $RI_{plus}$, referring to the positive terminal of the DC BUS, and one, indicated as $RI_{minus}$, referring to the negative terminal of the DC BUS.

Such insulation resistances represent leakage resistances toward ground distributed along the whole battery, through which small leakage currents pass due to an imperfect insulation between the active elements of the battery and the ground. Obviously, the leakage currents and the leakage resistances are spurious quantities, the result of unwanted parasitic phenomena, and therefore they should be ideally null.

For the sake of information completeness, in the model of the battery the parasitic capacitive components $CI_{minus}$ and $CI_{plus}$ are also indicated, which in fact are always present and are associated with the insulation resistances. Such capacitive components introduce a delay in the measurement operations, and theoretically should be considered for the purposes of the measurement of the insulation resistance.

When "Y" capacities have been placed between the DC BUS and the ground of the chassis in order to limit the electromagnetic emissions, they have a predefined and generally higher value than the parasitic capacitors $CI_{minus}$ and $CI_{plus}$, and therefore the delay due to the latter can be neglected.

If the aforesaid "Y" capacitors are not present, $CI_{minus}$ and $CI_{plus}$ are to be considered for the purposes of assessing the delays, and the presence thereof can be neglected, for the purposes of the calculations, only if the measurement acquisitions are performed after the exhaustion of the voltage transients caused by $CI_{minus}$ and $CI_{plus}$.

Figure 3:
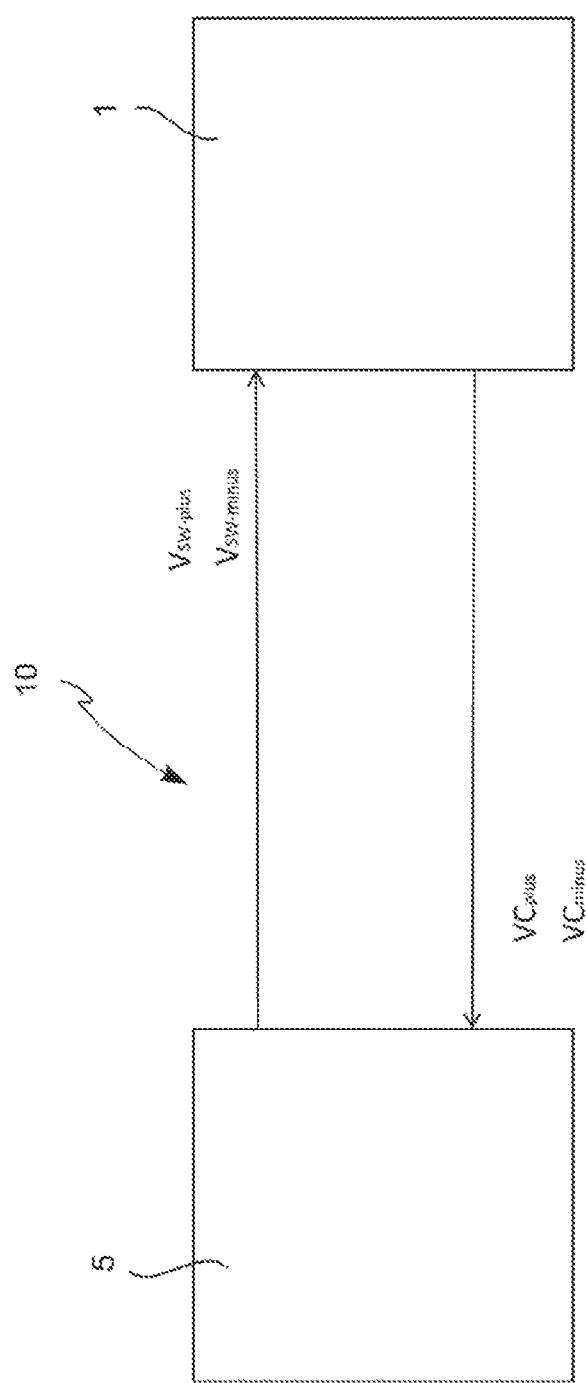
FIG. 3 shows a schematic diagram of a system employing the device in FIG. 1.

With reference to FIGS. 1 and 3, an electronic system 10 for the diagnosis of the insulation loss of an energized electrical apparatus (e.g., a battery) is now described.

Such a system 10 comprises an electronic device 1 according to any one of the embodiments shown above, for the diagnosis of the insulation loss of an energized electrical apparatus, and further comprises a control device 5.

The control device 5 generates and provides the first modulation switch SW1 with the aforesaid first driving signal $V_{SW-minus}$, and generates and provides the second modulation switch SW2 with the aforesaid second driving signal $V_{SW-plus}$.

Moreover, the control device 5 receives the first detection voltage $VC_{minus}$ from the first voltage meter $U_{minus}$ and the second detection voltage $VC_{plus}$ from the second voltage meter $U_{plus}$.

The control device 5 also determines a first value of first detection voltage $VC1_{plus}$, under condition of disconnection of the first sample resistance $RS_{minus}$, and determines a second value of first detection voltage $VC2_{minus}$, under condition of connection of the first sample resistance $RS_{minus}$.

The control device 5 is also configured to determine a first value of second detection voltage $VC1_{plus}$, under condition of disconnection of the second sample resistance $RS_{plus}$, and determines a second value of second detection voltage $VC2_{plus}$, under condition of connection of the second sample resistance $RS_{plus}$.

The control device 5 also calculates the negative terminal insulation resistance $RI_{minus}$ and the positive terminal insulation resistance $RI_{plus}$ of the energized electrical apparatus on the basis of the aforesaid first value of first detection voltage $VC1_{minus}$ and second value of first detection voltage $VC2_{minus}$ and/or of the aforesaid first value of second detection voltage $VC1_{plus}$ and second value of second detection voltage $VC2_{plus}$.

According to an implementation option of system 10, the control device 5 determines the first value of first detection voltage $VC1_{minus}$ on the basis of the first detection voltage maximum value $VC1_{minus-MAX}$ and the first detection voltage minimum value $VC1_{minus-MIN}$, under condition of disconnection of the first sample resistance $RS_{minus}$, and determines the second value of first detection voltage $VC2_{minus}$ on the basis of the first detection voltage maximum value $VC2_{minus-MAX}$ and the first detection voltage minimum value $VC2_{minus-MIN}$ under condition of connection of the first sample resistance $RS_{minus}$.

Similarly, the control device 5 determines the first value of second detection voltage $VC1_{plus}$ on the basis of the second detection voltage maximum value $VC1_{plus-MAX}$ and the second detection voltage minimum value $VC1_{plus-MIN}$ under condition of disconnection of the second sample resistance $RS_{plus}$, and determines the second value of second detection voltage $VC2_{plus}$ on the basis of the second detection voltage maximum value $VC2_{plus-MAX}$ and the second detection voltage minimum value $VC2_{plus-MIN}$ under condition of connection of the second sample resistance $RS_{plus}$.

According to an alternative implementation option, the determination of the aforesaid first or second value of first or second detection voltage is performed by the control device 5 on the basis of an average of samples detected by the respective signals.

According to one embodiment of the system, the aforesaid first driving signal $V_{SW-minus}$ is a pulse signal having a first frequency, in which the presence and absence of the pulse control the closing and opening, or the opening and closing, of the first modulation switch SW1, and in which the pulse duration with respect to period T associated with a first frequency defines a first close-open duty-cycle DC1. Similarly, the aforesaid second driving signal $V_{SW-plus}$ is a pulse signal having a second frequency, in which the presence and absence of the pulse control the closing and opening, or the opening and closing, of the second modulation switch SW2, and in which the pulse duration with respect to period T associated with the second frequency defines the second close-open duty-cycle DC2.

According to one embodiment, the control device 5 dynamically adjusts, during the measurement, one or any combination of the following parameters: first frequency of the first driving signal $V_{SW\text{-}minus}$; second frequency of the second driving signal $V_{SW\text{-}plus}$; first close-open duty-cycle DC1; second close-open duty-cycle (DC2).

In an implementing example, the first and the second driving signals $V_{SW\text{-}minus}$, $V_{SW\text{-}plus}$ are periodic signals of Pulse Width Modulation (PWM) type; the first and the second driving frequency are equal to each other; the first close-open duty-cycle DC1 and the second close-open duty-cycle DC2 are equal to each other.

Figure 4:
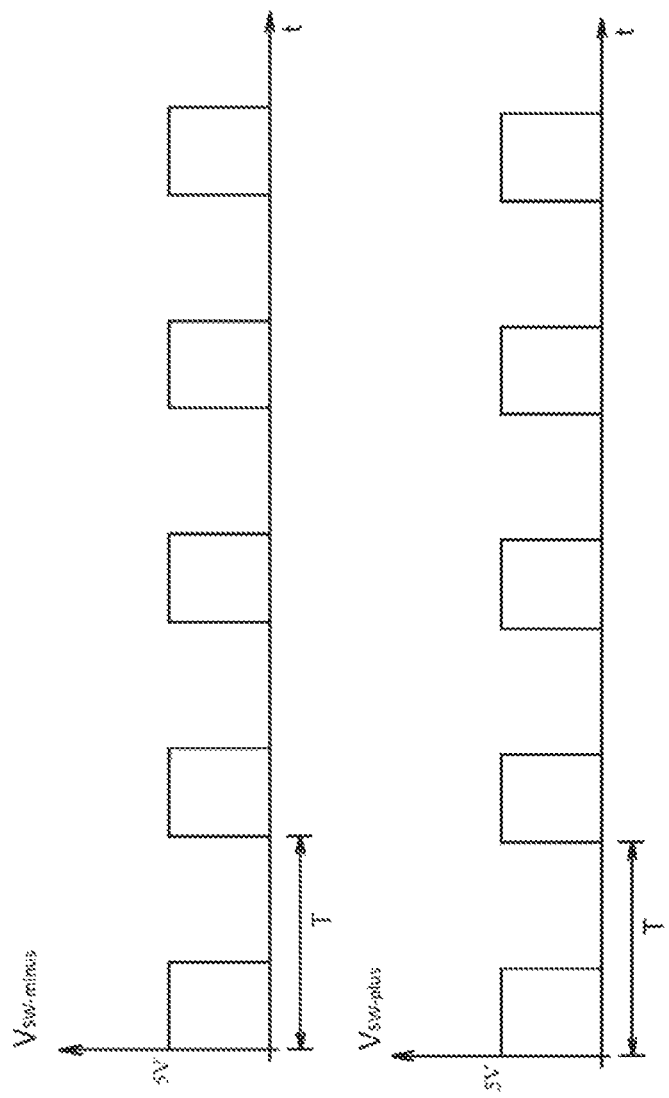
FIG. 4 depicts a diagram of driving signals used in the system of FIG. 3.

In a particular example, the driving signals $V_{SW\text{-}minus}$ and $V_{SW\text{-}plus}$ are identical or derive from a same signal. Such a circumstance is depicted by way of example in FIG. 4.

Considering now jointly FIGS. 1 and 3, the following further descriptive details are considered.

The measurement device 1 uses a kind of switching technique in each of the parts thereof.

Figure 2:
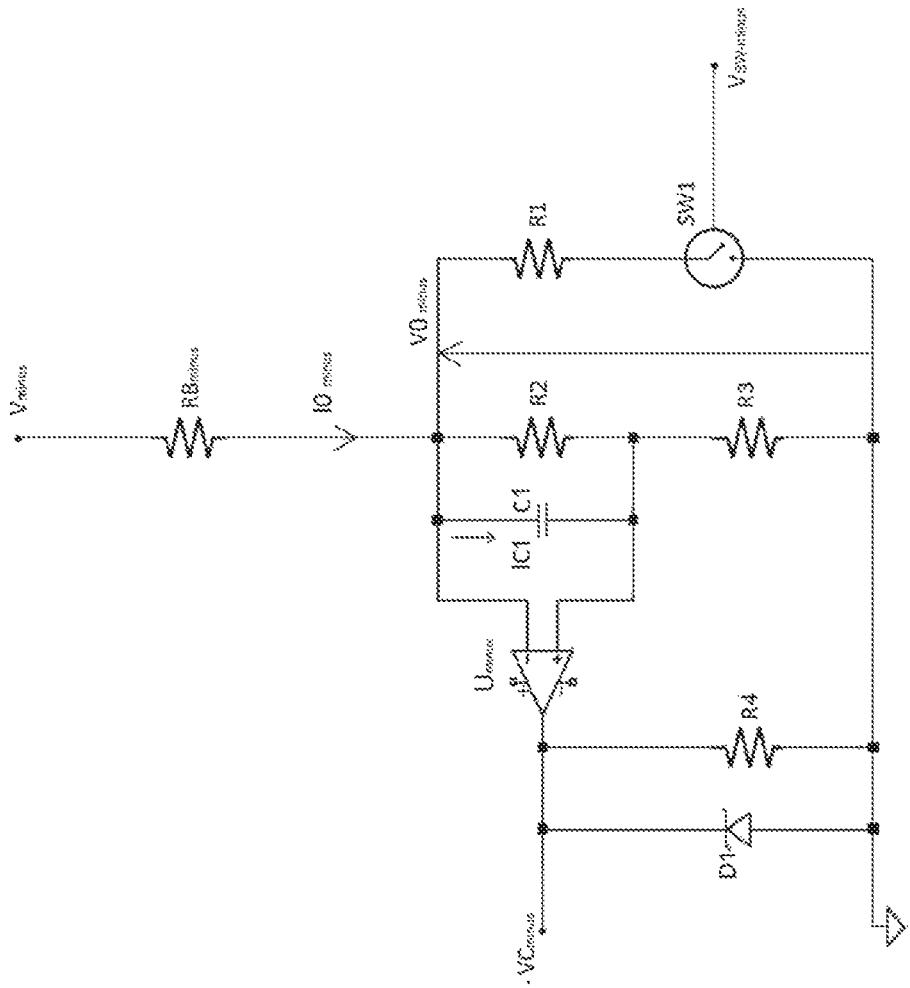
FIG. 2 schematically shows a portion of a device according to a further embodiment of the invention.

On the negative side of the battery, the measurement device 1 comprises, in the example herein contemplated, the resistors $RB_{minus}$, R1, R2, R3, capacitor C1, switch SW1 and an operational amplifier $U_{minus}$ in inverting configuration, which measures the voltage difference present at the ends of capacitor C1. Such a portion of the device is shown in FIG. 2.

Similarly, on the positive side of the battery, the measurement device 1 comprises, in the example herein considered, the resistors $RB_{plus}$, R5, R6, R7, capacitor C2, switch SW2 and the operational amplifier in inverting configuration, which measures the voltage difference present at the ends of capacitor C2.

The switches SW1 and SW2 are controlled by two driving signals of frequency type, references mentioned above, and indicated in FIG. 4 with numerals $V_{SW\text{-}minus}$ and $V_{SW\text{-}plus}$. In the simplest case, shown in FIG. 4, the two driving signals are PMW having frequency and duty-cycle which can be modified within a given range allowed: for example, the period may be of 2 ms with duty-cycle=50%, thus obtaining a square wave at a frequency of 500 Hz which is perfectly symmetrical with $T_{on}=T_{off}$.

With reference to the negative branch of the device (a similar disclosure applies mutatis mutandis for the positive branch), capacitor C1 serves to filter over time the voltage present at the ends of resistor R2; when switch SW1 is open, and therefore resistor R1 is excluded from the measurement circuit, the leakage current which crosses $RB_{minus}$ reaches the ground through resistance R2 and is partly intercepted by capacitor C1, which is therefore charged, thus increasing the voltage at the ends thereof. Instead, when switch SW1 is closed, resistor R1, which has a significantly lower value with respect to R2, is arranged in parallel to the series consisting of R2 and R3; accordingly, the resistance of that parallel decreases and capacitor C1 starts to be discharged.

The charging and discharging cycle of capacitor C1 repeats periodically, stabilizing around a position of equilibrium, or stationary steady state, after a given transient.

The average voltage at the ends of capacitor C1 and of resistor R2 depends on the current which crosses resistor $RB_{minus}$ and on a proportionality factor which is dependent on the relative value of resistor R2 with respect to resistor R1 and R3 and on the duty-cycle with which switch SW1 is driven. The current which crosses resistance $RB_{minus}$ is in turn proportional to voltage $V_{minus}$ of the negative pole of the battery pack with respect to ground. Therefore, the voltage at the ends of capacitor C1 and the voltage $VC_{minus}$ acquired by the insulation resistance measurement system is proportional to voltage $V_{minus}$.

Advantageously, this may result in the proportionality factor between $VC_{minus}$ and $V_{minus}$ being dynamically varied (for example by varying the duty-cycle) according to the voltages measured, when required. On the contrary, in known measurement methods, the proportionality factor between $VC_{minus}$ and $V_{plus}$ is constant over time and cannot be changed once the measurement circuit is defined.

The switching period of switch SW1 can be selected so as to be lower than the time constants due to the parasitic parameters present in the circuit of the battery (this is true, for example, for a switching period equal to 2 ms). Thereby, the charge and discharge of capacitor C1 has an approximately linear trend over time.

Figure 5:
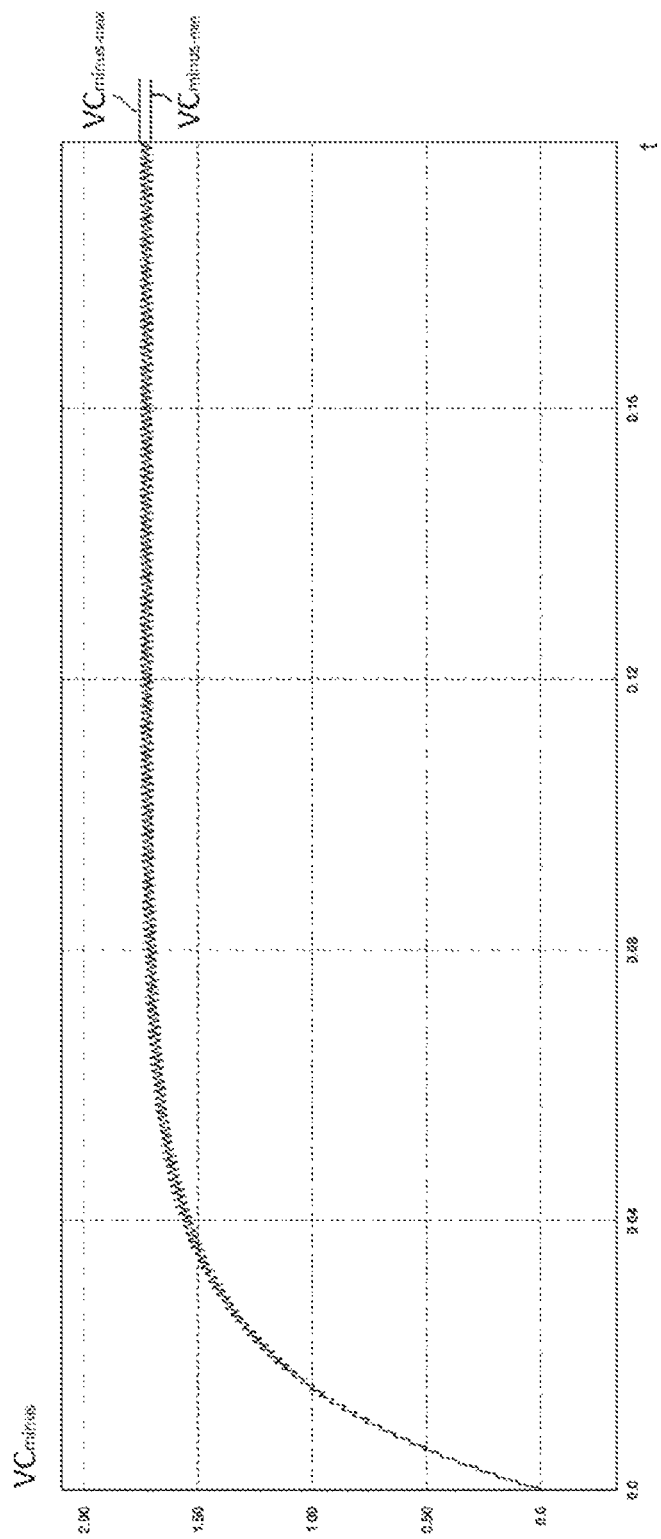
FIGS. 5 and 6 depict example time diagrams of the evolution of voltage signals detected by the device of the invention and used by the measurement method according to the invention.

Therefore, once a condition of the equilibrium is reached during the measurement, when the voltages $V_{minus}$ and $V_{plus}$ are stabilized by reaching a steady state, a triangular-shaped signal is present at the ends of capacitor C1 oscillating between two values, the maximum of which is reached at the end of the charge and the minimum of which is reached at the end of the discharge, thus causing an overall time evolution like the one shown by way of example in FIG. 5 (with reference to $V_{minus}$; it is also worth noting that $V_{plus}$ has a similar trend).

The average value of each of the voltages $VC_{minus}$ and $VC_{plus}$ can easily be obtained, for example, by alternatively sampling the respective signal on the maximum value and on the minimum value.

The voltages $VC_{minus}$ and $VC_{plus}$ are directly proportional to the negative and positive voltages of the battery with respect to ground. Therefore, when the measurement has stabilized, at steady-state, $VC_{minus}$ and $VC_{plus}$ also indirectly depend on the unknown value of the insulation resistances $RI_{minus}$, $RI_{plus}$, besides depending on the known resistances and duty-cycles of the measurement circuits.

The considerations hereinto made refer to the case when the two switches $S_{minus}$ and $S_{plus}$ are both kept open.

The effect obtained following the activation of such switches will be described later to illustrate the measurement method of the present invention.

In various embodiments, system 10 performs measurement methods and diagnoses, and/or operates self-diagnosis procedures as described later.

A method is now described for measuring the negative terminal insulation resistance $RI_{minus}$, present between a negative terminal 11 and the ground 3 of an energized electrical apparatus 2, and the positive terminal insulation resistance $RI_{plus}$, present between a positive terminal 12 and ground 3 of the same energized electrical apparatus 2.

In a typical application example, such a ground 3 is a "main" ground of the motor vehicle, for example the chassis of the motor vehicle itself.

The method firstly comprises the steps of connecting a first measurement circuit 15 between the aforesaid negative terminal 11 and ground 3 of the energized electrical apparatus 2 to detect a first value $VC1_{minus}$ of a first detection voltage $VC_{minus}$, depending on the negative voltage $V_{minus}$ of the energized electrical apparatus 2; furthermore, connecting a second measurement circuit 16 between the aforesaid positive terminal 12 and ground 3 of the energized electrical apparatus 2 to detect a first value $VC1_{plus}$ of a second detection voltage $VC_{plus}$, depending on the positive voltage $V_{plus}$ of the energized electrical apparatus 2.

Then, the method comprises one of the following two alternative steps: connecting a first sample resistance $RS_{minus}$ in parallel to the first measurement circuit 15, between the aforesaid negative terminal 11 and ground 3; or connecting a second sample resistance $RS_{plus}$ in parallel to the second measurement circuit 16, between the aforesaid positive terminal 12 and ground 3.

The method then provides detecting a second value $VC2_{minus}$ of the first detection voltage $VC_{minus}$ and detecting a second value $VC2_{plus}$ of the second detection voltage $VC_{plus}$ under the aforesaid connection condition of connection of one between the first sample resistance $RS_{minus}$ and the second sample resistance $RS_{plus}$.

Finally, the method comprises the step of calculating the negative terminal insulation resistance $RI_{minus}$ and the positive terminal insulation resistance $RI_{plus}$ of the energized electrical apparatus on the basis of the aforesaid first value of first detection voltage $VC1_{plus}$, second value of first detection voltage $VC2_{minus}$, first value of second detection voltage $VC1_{plus}$ and second value of second detection voltage $VC2_{plus}$.

The aforesaid step of detecting a first value of first detection voltage $VC1_{minus}$ comprises the steps of: modulating the first detection voltage $VC_{minus}$ by a modulation signal; then detecting the modulated first detection voltage $VC_{minus}$; then determining the first value of first detection voltage $VC1_{minus}$ on the basis of the modulated first detection voltage $VC_{minus}$.

The aforesaid step of detecting a first value of second detection voltage $VC1_{plus}$ comprises the steps of: modulating the second detection voltage $VC_{plus}$ by a modulation signal; then detecting the modulated second detection voltage $VC_{plus}$; then determining the first value of second detection voltage $VC1_{plus}$ on the basis of the modulated second detection voltage $VC_{plus}$.

The aforesaid step of detecting a second value of first detection voltage $VC2_{minus}$ comprises the steps of: modulating again the first detection voltage $VC_{minus}$ by the modulation signal while the aforesaid first sample resistance $RS_{minus}$ or second sample resistance $RS_{plus}$ is connected; then detecting again the modulated first detection voltage $VC_{minus}$ and determining the second value of first detection voltage $VC2_{minus}$ on the basis of the modulated first detection voltage $VC_{minus}$ detected while the aforesaid first sample resistance $RS_{minus}$ or second sample resistance $RS_{plus}$ is connected.

The aforesaid step of detecting a second value of second detection voltage $VC2_{plus}$ comprises the steps of: modulating again the second detection voltage $VC_{plus}$ by the modulation signal while the aforesaid first sample resistance $RS_{minus}$ or second sample resistance $RS_{plus}$ is connected; then detecting again the modulated second detection voltage $VC_{plus}$ and determining a second value of second detection voltage $VC2_{plus}$ on the basis of the modulated second detection voltage $VC_{plus}$ detected while the aforesaid first sample resistance $RS_{minus}$ or second sample resistance $RS_{plus}$ is connected.

According to one particular embodiment, prior to the aforesaid step of connecting the first or second sample resistance, the method provides comparing the first value of first detection voltage $VC1_{minus}$ with the first value of second detection voltage $VC_{plus}$; if the comparison results in the first detection voltage $VC_{minus}$ being greater than the second detection voltage $VC_{plus}$, the first sample resistance $RS_{minus}$ is connected; if instead the comparison results in the first detection voltage $VC_{minus}$ being less than the second detection voltage $VC_{plus}$, the second sample resistance $RS_{plus}$ is connected.

The above-described embodiment advantageously allows performing the measurement procedure which implies reaching smaller voltages in absolute value (see for example, FIG. 6), which reduces possible criticalities.

According to an implementation option of the method, the aforesaid step of modulating the first detection voltage $VC_{minus}$ comprises modulating the first detection voltage $VC_{minus}$ so that it oscillates between a first detection voltage maximum value $VC1_{minus-MAX}$ and a first detection voltage minimum value $VC1_{minus-MIN}$.

The aforesaid the step of modulating again the first detection voltage $VC_{minus}$ comprises modulating again the first detection voltage $VC_{minus}$ so that it oscillates between a new first detection voltage maximum value $VC2_{minus-MAX}$ and a new first detection voltage minimum value $VC2_{minus-MIN}$.

The aforesaid step of modulating the second detection voltage $VC_{plus}$ comprises modulating the second detection voltage $VC_{plus}$ so that it oscillates between a second detection voltage maximum value $VC1_{plus-MAX}$ and a second detection voltage minimum value $VC1_{plus-MIN}$.

The aforesaid step of modulating again the second detection voltage $VC_{plus}$ comprises modulating the second detection voltage $VC_{plus}$ so that it oscillates between a new second detection voltage maximum value $VC2_{plus-MAX}$ and a new second detection voltage minimum value $VC2_{plus-MIN}$.

It is worth noting that the insulation resistance measurement method described above provides various implementing options concerning how to perform the steps of detecting the first or second detection voltage and of determining the first and the second value of such a first or second detection voltage.

According to one implementing option, the aforesaid step of detecting a modulated first detection voltage $VC_{minus}$ comprises measuring the first detection voltage maximum value $VC1_{minus-MAX}$ and the first detection voltage minimum value $VC1_{minus-MIN}$; and determining a first value of first detection voltage $VC1_{minus}$ on the basis of the first detection voltage maximum value $VC1_{minus-MAX}$ and the first detection voltage minimum value $VC1_{minus-MIN}$.

Similarly, the aforesaid step of detecting again a modulated first detection voltage $VC_{minus}$ comprises measuring the first detection voltage maximum value $VC2_{minus-MAX}$ and the first detection voltage minimum value $VC2_{minus-MIN}$ while the first sample resistance $RS_{minus}$ or the second sample resistance $RS_{plus}$ is connected, and then determining a second value of first detection voltage $VC2_{minus}$ on the basis of said first detection voltage maximum value $VC2_{minus-MAX}$ and first detection voltage minimum value $VC2_{minus-MIN}$ detected while the first sample resistance $RS_{minus}$ or the second sample resistance $RS_{plus}$ is connected.

Moreover, the aforesaid step of detecting a second detection voltage $VC_{plus}$ comprises measuring the second detection voltage maximum value $VC1_{plus-MAX}$ and the second detection voltage minimum value $VC1_{plus-MIN}$, and determining a first value of second detection voltage $VC1_{plus}$ on the basis of the second detection voltage maximum value $VC1_{plus-MAX}$ and the second detection voltage minimum value $VC1_{plus-MIN}$.

Similarly, the aforesaid step of detecting again a modulated second detection voltage $VC_{plus}$ comprises measuring the second detection voltage maximum value $VC2_{plus-MAX}$ and the second detection voltage minimum value $VC2_{plus-MIN}$ while the first sample resistance $RS_{minus}$ or the second sample resistance $RS_{plus}$ is connected; and then determining a second value of second detection voltage $VC2_{plus}$ on the basis of said second detection voltage maximum value $VC2_{plus-MAX}$ and second detection voltage minimum value $VC2_{plus-MIN}$ detected while the first sample resistance $RS_{minus}$ or the second sample resistance $RS_{plus}$ is connected.

According to an alternative implementing option, the aforesaid steps of detecting a first or a second detection voltage comprise detecting a sequence of samples of the modulated first or second detection voltage; and the successive steps of determining a first or second value of first or second detection voltage comprise determining an average value of the samples respectively detected.

Preferably, the aforesaid measurements are performed in a stationary steady state, i.e., after a settlement time following the transient occurring each time branches of the circuit are connected or disconnected.

In this regard, the measurement of the detected signal samples also may be employed to check the end of the transient or recognize the achievement of the stationary steady state.

More precise details will be provided later concerning a further implementing example of the measurement method, in conjunction with an explicative mathematical disclosure aiming to clarify the relations between the various quantities involved.

Reference is made for example, to FIG. 2, which shows a portion of the "negative branch" of device 1 related to voltage $V_{minus}$ (similar arguments and illustrations apply to the "positive branch" of device 1 related to voltage $V_{plus}$).

To determine the relation between $V_{minus}$ and $VC_{minus}$, you may begin by calculating the voltage oscillation $\Delta VC_{minus}$ (equal to $VC1_{minus-MAX} - VC1_{minus-MIN}$) generated by the current which charges and discharges capacitor C1 due to the effect of opening and closing switch SW1 (with periods $T_{ON}$ and $T_{OFF}$).

$$\Delta VC_{minus}|_{ON} = \frac{1}{C_1} I_{C1\_ON} * T_{ON} = -\Delta V_{C_{minus}}|_{OFF} = -\frac{1}{C_1} I_{C1\_OFF} * T_{OFF} \quad (1)$$

relation valid in the hypothesis that the charge and discharge constant of the capacitor is much greater than the times $T_{ON}$ and $T_{OFF}$.

By indicating as $I0_{minus}$ the current which crosses the partition resistance $RB_{minus}$, the current which crosses capacitor C1 when switch SW1 is closed is:

$$I_{C1_{ON}} = \frac{R_1 R_2 I0_{minus} - VC_{minus}(R_1 + R_2 + R_3)}{R_1 R_2 + R_2 R_3}$$

Instead, when switch SW1 is open, and therefore resistance R1 is disconnected from the circuit, the current which crosses capacitor C1 is:

$$I_{C1_{OFF}} = I0_{minus} - \frac{VC_{minus}}{R_2}$$

Moreover, let's consider the definition of Duty=$T_{ON}/(T_{ON}+T_{OFF})$. Such a parameter corresponds to the parameters DC1 or DC2, already mentioned above.

By replacing $I_{C1_{ON}}$, $I_{C1_{OFF}}$ and Duty in the relation (1), the following is obtained:

$$I0_{minus} = \frac{R_1 + R_2 * \text{Duty} + R_3}{R_1 R_2 + R_2 R_3 (1 - \text{Duty})} VC_{minus} \quad [2]$$

By indicating as $V0_{minus}$ the partitioned voltage present at the negative terminal of the inverting operational $U_{minus}$, $V0_{minus}$ may be determined according to voltage $VC_{minus}$ and current $I0_{minus}$ when switch SW1 is closed (phase ON):

$$V0_{minus} = \left(I0_{minus} - \frac{V0_{minus} - VC_{minus}}{R_3}\right) R_1 \rightarrow$$

$$V0_{minus} = \frac{(I0_{minus} R_1 R_3 + VC_{minus} R_1)}{(R_1 + R_3)}$$

Noting that $V_{minus} = RB_{minus} I0_{minus} V0_{minus}$, an expression is obtained for $V_{minus\_ON}$.

$$V_{\_minus\_on} \frac{I0_{minus} R_1 R_3 + VC_{minus} R_1}{R_1 + R_3} + RB_{minus} I0_{minus}$$

Similarly, using the same expression, by making the limit for R1 tending to infinite, the value $V_{minus}$ OFF, valid in the case of phase OFF, with SW1 open, is obtained.

$$V_{\_minus\_off} = I0_{minus} R_3 + VC_{minus} + RB_{minus} I0_{minus}$$

Voltage $V_{minus}$ can be expressed as $$V_{\_minus} = \text{Duty} * V_{\_minus\_on} + (1-\text{Duty}) * V_{\_minus\_off}$$

For calculation simplicity, by way of example, consider the case in which Duty=50%:

$$V_{\_minus} = 0.5 * V_{\_minus\_on} + 0.5 * V_{\_minus\_off} = \frac{V_{\_minus\_on} + V_{\_minus\_off}}{2}$$

which, by solving $V_{minus}$ ON and $V_{minus}$ OFF and developing the algebraic expression, becomes:

$$V_{\_minus} = I0_{minus} \frac{R_1 R_3 + R_1 + 2 RB_{minus}(R_1 + R_3) + R\frac{2}{3}}{2(R_1 + R_3)} + VC_{minus} \frac{2R_1 + R_3}{2(R_1 + R_3)}$$

Replacing the above-indicated expression [2] in such an expression results in:

$$V_{\_minus} = \quad (3a)$$
$$VC_{minus} \left( \frac{2R_1 + 2R_3 + R_2}{R_2(2R_1 + R_3)} * \frac{2R_1 R_3 + R_3^2 + 2RB_{minus}(R_1 + R_3)}{2(R_1 + R_3)} + \frac{2R_1 + R_3}{2(R_1 + R_3)} \right)$$

With an entirely similar procedure, the following is obtained:

$$V_{\_plus} = VC_{plus}\left(\frac{2R_5 + 2R_7 + R_6}{R_6(2R_5 + R_7)} * \right. \tag{3b}$$

$$\left. \frac{2R_5R_7 + R_7^2 + 2RB_{plus}(R_5 + R_7)}{2(R_5 + R_7)} + \frac{2R_5 + R_7}{2(R_5 + R_7)}\right)$$

As noted above, amplifier $U_{minus}$ is in inverting configuration with unitary gain so as to obtain a positive quantity output with respect to the ground of the chassis. Therefore, starting from an electrical quantity $V_{minus}$, which is negative with respect to the voltage of the chassis, a negative voltage $VC_{minus}$ at the amplifier input and a positive voltage $-VC_{minus}$ at the output of the same amplifier, are obtained.

On the contrary, amplifier $U_{plus}$ is in non-inverting configuration since $V_{plus}$ is already positive with respect to the voltage of the chassis.

When the two branches of the device are made in a symmetrical manner, $RB_{plus} = RB_{minus} = RB$, and moreover: $R5 = R1$, $R6 = R2$, $R7 = R3$.

In this case, the equations (3a) and (3b) become:

$$V_{\_plus} =$$
$$VC_{plus}\left(\frac{2R_1 + 2R_3 + R_2}{R_2(2R_1 + R_3)} * \frac{2R_1R_3 + R_3^2 + 2RB(R_1 + R_3)}{2(R_1 + R_3)} + \frac{2R_1 + R_3}{2(R_1 + R_3)}\right)$$

$$V_{\_minus} =$$
$$V_{c\_minus}\left(\frac{2R_1 + 2R_3 + R_2}{R_2(2R_1 + R_3)} * \frac{2R_1R_3 + R_3^2 + 2RB(R_1 + R_3)}{2(R_1 + R_3)} + \frac{2R_1 + R_3}{2(R_1 + R_3)}\right)$$

Defining $$\left(\frac{2R_1 + 2R_3 + R_2}{R_2(2R_1 + R_3)} * \frac{2R_1R_3 + R_3^2 + 2RB(R_1 + R_3)}{2(R_1 + R_3)} + \frac{2R_1 + R_3}{2(R_1 + R_3)}\right) = A$$

the following simplified formulae are obtained:

$$V_{\_plus} = VC_{plus} * A$$

$$V_{\_minus} = VC_{minus} * A$$

$$V_{\_plus} - V_{\_minus} = (VC_{plus} - VC_{minus}) * A \tag{4}$$

Formula (4) shows that it is always possible to determine the value of $V_{minus}$ from the measurement of $VC_{minus}$, and the value of $V_{plus}$ from the measurement of $VC_{plus}$, and the sum of which, in absolute value, is the battery voltage $V_B$.

However, from the determination of $V_{minus}$ and $V_{plus}$, it is still not possible to calculate the value of the two insulation resistances because, according to the hypotheses made, the two equations (3a) and (3b) are linearly dependent on each other. To be able to calculate the value of the two insulation resistances $RI_{plus}$ and $RI_{minus}$, a further measurement is performed of $V_{minus}$ and of $V_{plus}$ after inserting in the measurement circuit at least one of the two resistors $RS_{minus}$ or $RS_{plus}$, which value is known, by closing of the respective switches $S_{minus}$ or $S_{plus}$.

It is worth noting that in expression (4), all the parameters are known: A is known because it is a design datum dependent on the value of the resistances selected for the measurement circuit and the Duty and on the state of the switches $S_{minus}$ or $S_{plus}$; $VC_{minus}$ and $VC_{plus}$ are acquired by the insulation resistance measurement system; the difference $V_{plus} - V_{minus}$ is the voltage of BUS DC or of battery, which is acquired separately.

Therefore, unless there is a measurement error, it is always possible to perform an analysis of the consistency between the values $VC_{plus} - VC_{minus}$ acquired by the insulation resistance measurement system and the battery voltage $V_B = V_{plus} - V_{minus}$ independently acquired by the acquisition circuit of the battery voltage signals of the BMS. Thereby, gain or offset errors present in the measurement circuit of the insulation resistance can be diagnosed in advance (is worth noting that this is one of the possible self-diagnosis tests, which will be described later).

The value of the sample resistances $RS_{minus}$ and $RS_{plus}$ (which may be connected and disconnected to/from the negative pole and to/from the positive pole of the battery, respectively, with respect to the ground of the chassis) preferably shall conform with the provisions set out in Standard ISO 6469, while taking into consideration also the presence in parallel of the two resistances of the measurement circuit. In particular, the value of resistance $RS_{minus}$ preferably takes on a value dependent on the battery voltage $V_B$ so that the parallel of RS with RB ranges from about 100 ohm/V to about 500 ohm/V.

By inserting one of the resistances $RS_{minus}$, $RS_{plus}$ into the measurement circuit through the respective switches $S_{plus}$, $S_{minus}$, the voltages $V_{minus}$ and $V_{plus}$ can be unbalanced with respect to the ground and a new measurement of such voltages can be obtained with respect to the ground through the acquisition of the voltages $VC_{minus}$ and $VC_{plus}$.

Since all the electronic components forming the measurement circuit of the insulation resistance have known values, the value of the insulation resistance of the battery can be obtained with respect to the ground of the chassis from the measurement of $VC_{minus}$ and of $VC_{plus}$ before and after the closing of one of the two switches $S_{plus}$ and $S_{minus}$. Moreover, a more and more accurate estimate of the two insulation resistances can be obtained through the periodic acquisition of the voltages $VC_{minus}$ and of $VC_{plus}$.

Figure 6:
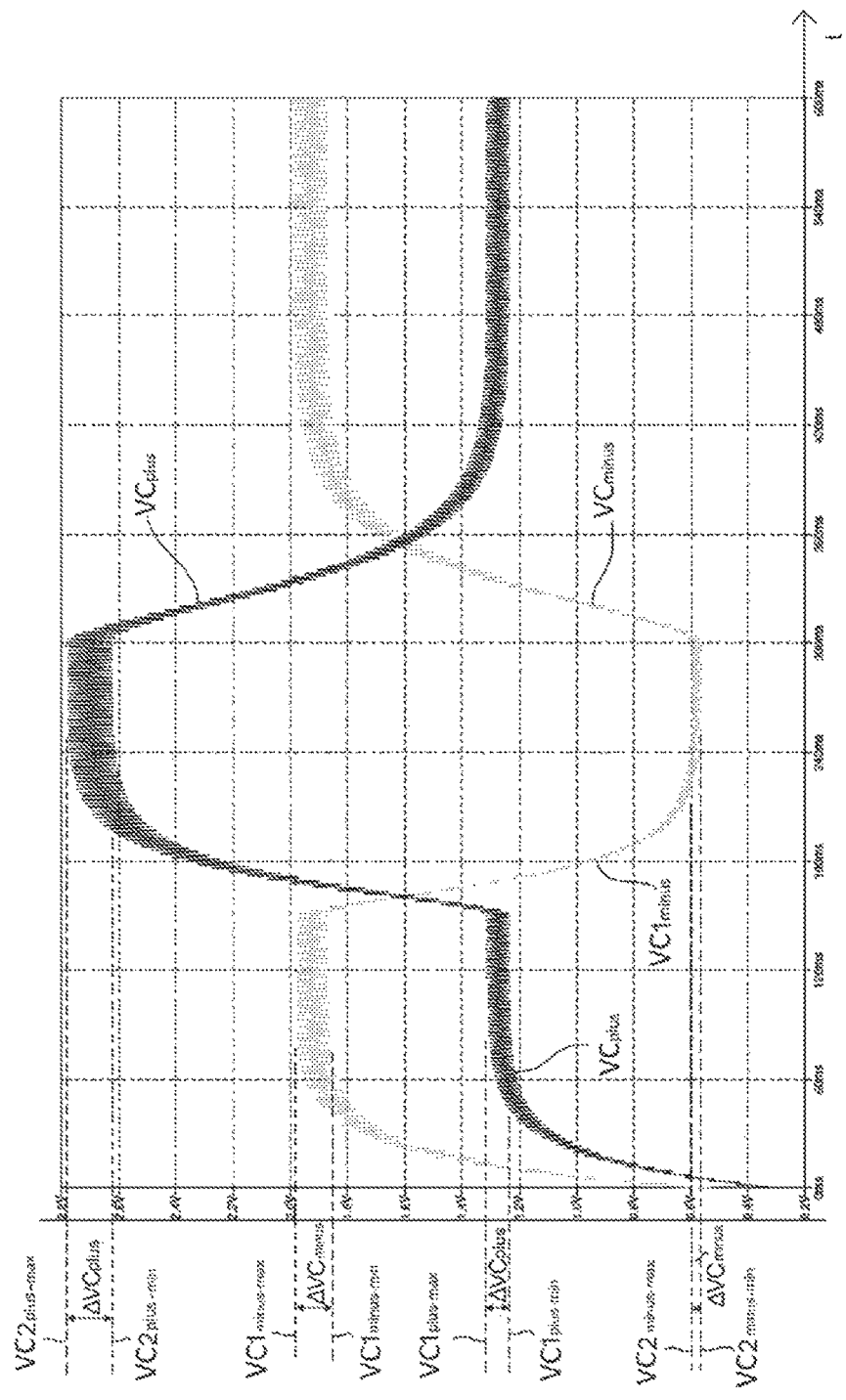

According to an implementing example, the procedure employed and the time evolution of the voltages $VC_{minus}$ and $VC_{plus}$ during the closing of one of the two switches $S_{plus}$ and $S_{minus}$ are depicted in FIG. 6, as described herein below.

To perform the estimate of the value of the insulation resistances $RI_{plus}$ and $RI_{minus}$ (which may occur in an almost continuous manner during the functioning of the system), a first acquisition of the voltages $VC_{minus}$ and $VC_{plus}$ is performed with the two switches $S_{minus}$ and $S_{plus}$ open. Then, one of the two switches $S_{plus}$ or $S_{minus}$ is closed depending on whether $VC_{minus}$ is greater or less than $VC_{plus}$. Then, the stabilization of the two values to be acquired is awaited, and then a new acquisition is performed of the values $VC_{minus}$ and $VC_{plus}$. After the double measurement, a first estimate of the value of the two insulation resistances $RI_{plus}$ and $RI_{minus}$ can be obtained.

Such a procedure may be performed periodically in order to improve the precision and reliability of the measurement over time.

FIG. 6 shows, by way of example, the trend of the two voltages $VC_{minus}$ and $VC_{plus}$ acquired during the calculation procedure of the insulation resistances. In this specific case, it is assumed that $RI_{minus} > RI_{plus}$, therefore in the first step, in which the two switches $S_{plus}$ and $S_{minus}$ are open, voltage $VC_{minus}$ is greater than $VC_{plus}$. This results in switch $S_{minus}$ being closed in the second measurement step, putting in parallel resistance $RI_{minus}$ to resistance $RS_{minus}$, the closing of which converts the unbalancing of the two voltages, and a successive measurement is performed of the two voltages $VC_{minus}$ and $VC_{plus}$ at the end of the transient. The value of the two insulation resistances is obtained from the measurements obtained through the two acquisitions, through a known conversion formula, which is indicated herein below.

FIG. 6 also points out the oscillations of the two signals $VC_{minus}$ and $VC_{plus}$, which are due to the imposed modulation, and therefore the values $VC1_{minus-max}$, $VC1_{minus-min}$, $VC1_{plus-max}$ and $VC1_{plus-min}$ (within which $VC_{minus}$ and $VC_{plus}$ oscillate, respectively, in the circumstance in which resistance $RS_{minus}$ is not connected) and the values $VC2_{minus-max}$, $VC2_{minus-min}$, $VC2_{plus-max}$ and $VC2_{plus-min}$ (within which $VC_{minus}$ and $VC_{plus}$ oscillate, respectively, in the circumstance in which resistance $RS_{minus}$ is connected), are indicated.

Herein below is described a possible algorithm for the calculation of the insulation resistances.

$RB'_{minus}$ indicates the sum of resistance $RB_{minus}$ and of the equivalent resistance of the measurement circuit consisting of resistances R1, R2, R3 and of capacitor C1 (also affected by the control Duty of SW1):

$$RB'_{minus} = RB_{minus} + \frac{V0_{minus}}{I0_{minus}}$$

The case is considered in which $VC_{minus}$ is greater than $VC_{plus}$, after the first acquisition step. In this case, switch $S_{minus}$ is closed and a new value of $VC_{minus}$ is acquired. Once the new value of $VC_{minus}$ is known, the current which crosses the measurement circuit $I0_{minus}$ is recalculated using the aforesaid equation [1].

Once $I0_{minus}$ and $VC_{minus}$ are known, similarly to that shown above, $V0_{minus-ON}$, $V0_{minus-OFF}$, and $V0_{minus}$ are recalculated. Thus a new estimate of $V_{minus}$ is obtained, which is indicated with $V'_{minus}$:

$$V'_{minus} = -RB_{minus} I0_{minus} + V0_{minus}$$

By indicating as RB2, the parallel between $RB'_{minus}$ and $RS_{minus}$:

$$RB2 = \frac{RB'_{minus} * RS_{minus}}{RB'_{minus} + RS_{minus}}$$

and substituting the expressions obtained above in the expressions [3a] and [3b], two algebraic relations are reached which allow calculating the values of the insulation resistances $$RI_{minus} = \frac{RB'_{minus} * RB2 * VBATT * (V_{minus} - V'_{minus})}{RB'_{minus} * VBATT * V'_{minus} - RB2 * VBATT * V_{minus} + RB'_{minus} * V_{minus} * V'_{minus} - RB2 * V_{minus} * V'_{minus}}$$

$$RI_{plus} = \frac{RB'_{minus} * RB2 * VBATT * (V\__{minus} - V'\__{minus})}{RB'_{minus} * VBATT * V_{minus} - RB2 * VBATT * V'_{minus} + RB'_{minus} * V\__{minus} * V'_{minus} - RB2 * V\__{minus} * V'_{minus}}$$

Similarly, if $VC_{minus}$ were less than $VC_{plus}$, $S_{plus}$ would be closed and the following calculation would be obtained:

$$RI_{minus} = \frac{RB'_{plus} * RB2 * VBATT * (V_{plus} - V'_{plus})}{RB2 * VBATT * V'_{plus} - RB2 * VBATT * V_{plus} + R'_{B_{plus}} * V_{plus} * V'_{plus} - RB2 * V_{plus} * V'_{plus}}$$

$$RI_{plus} = \frac{R'_{B_{minus}} * RB2 * VBATT * (V_{plus} - V'_{plus})}{RB'_{plus} * VBATT * V'_{plus} - RB2 * VBATT * V_{plus} + RB'_{plus} * V_{plus} * V'_{plus} - RB2 * V_{plus} * V'_{plus}}$$

A method for diagnosing an insulation loss of an energized electrical apparatus 2 is now described.

Such a method comprises the steps of measuring a negative terminal insulation resistance $RI_{minus}$, present between a negative terminal 11 and the ground 3 of the energized electrical apparatus 2, and a positive terminal insulation resistance $RI_{plus}$, present between a positive terminal 12 and the ground 3 of the energized electrical apparatus; and therefore diagnosing the insulation loss of the energized electrical apparatus 2 on the basis of the negative terminal insulation resistance $RI_{minus}$ and the positive terminal insulation resistance $RI_{plus}$ which have been measured.

In such a diagnosis method, the aforesaid measurement step is performed by an insulation resistance measurement method according to one of the embodiments shown above.

Herein below, aspects will be shown, that are associated with the functions of self-diagnosis, which the device and the system of the invention are capable of performing, with the aim to ensure and check the integrity of the circuit for the measurement of insulation. Such functions comprise a group of tests having the task to periodically check the integrity of the measurement circuit of the insulation resistance.

The execution of such tests may occur according to a pre-ordered sequence, between one insulation resistance measurement and another, or according to the result of preceding tests or according to the functioning state of the system at a given moment.

The self-diagnosis functions may comprise any subgroup of tests herein below shown, by way of example, or other similar tests: indeed, given the flexibility of the measurement circuit, it is theoretically possible to perform many different tests, some of which perfectly equivalent to one other; only the simplest or most significant tests are described here.

The tests which may be executed are substantially "plausibility tests", which are performed under particular operating conditions of the device, and are capable of checking the correspondence or lack of correspondence between a value read and a respective value expected.

Let's consider the functioning self-diagnosis of the device switches $M_{minus}$, $M_{plus}$ having the task to check the integrity of the two device switches, or relays, which allow the connection and disconnection of the insulation resistance measurement circuit to/from the poles of the battery. Whether they are of the electrical-mechanical type or they are made by electronic technology (for example, solid-state relays, photoMOS, MOSFET, and so on), such relays are often subjected to electrical stress and they may be damaged. When the two device switches are open, the measurement device is disconnected from the battery and it is not supplied; therefore, the voltages $VC_{minus}$ and $VC_{plus}$ are to be almost null. When the two device switches instead are closed, the measurement device is connected to the battery and it is supplied; therefore, the voltages $VC_{minus}$ and $VC_{plus}$ are to have values the sum of which is proportional to the battery voltage and to the duty cycle applied to the measurement device, which, in extreme cases, may also be null (when switch SW1 is always open) or unitary (when switch SW1 is always closed).

Let's consider now the functioning self-diagnosis of the first resistance-switch group ($RB_{minus}$, $S_{minus}$) and of the second resistance-switch group ($RS_{plus}$, $S_{plus}$).

Such a self-diagnosis in particular comprises a test for checking the integrity of the two input switches (or relays) of sample resistance $S_{plus}$ and $S_{minus}$. Whether they are of electromechanical type or electronic type, these relays must support high potential differences at the ends thereof and are frequently subjected to electrical stresses which may damage them.

Here, the checking test may for example, consist in controlling the two input switches of sample resistance $S_{plus}$ and $S_{minus}$ sequentially in the four configurations possible and, for each one, reading the value either of $VC_{minus}$ or of $VC_{plus}$ or of both, and performing certain plausibility tests on the basis of the values read.

Let's consider now a self-diagnosis of integrity of the device based on a consistency test on the gain. Such a test is based on the fact that the sum of the voltages $VC_{plus}$ and $VC_{minus}$ is associated with the battery voltage $V_B$ through a proportionality factor indicated with A, which depends on the duty. In particular, the following relation applies:

$$VC_{plus} - VC_{minus} = A*(V_{plus} + V_{minus}),$$

in which A is the attenuation of the acquisition circuit.

The self-diagnosis test of the gain comprises a group of safety mechanisms capable of detecting faults which may result in an incorrect estimate of the battery voltage, which is partitioned in the two voltages $VC_{plus}$ and $VC_{minus}$ referring to the ground, the occurrence of any condition which modifies the gain of the measurement circuit (for example, a variation of the resistances $RB_{minus}$ or $RB_{plus}$ or a gain error of the amplifiers $U_{minus}$ or $U_{plus}$). Such a test may provide for example comparing the value of voltage $V_B$ acquired through the insulation measurement device with respect to the direct measurement of the battery voltage $V_B$, which is a piece of information available through other measurement circuits.

Let's consider now the self-diagnosis of the modulation switches SW1 and SW2, which aims to check the correct operation of such switches by checking the presence and the amplitude of the modulation oscillation on the signals $VC_{minus}$ and $VC_{plus}$. The signals $VC_{plus}$ and $VC_{minus}$ are measured (upon prior checking that any transients on such signals are concluded) at each switching front of SW1 and SW2, and it is observed whether the modulation oscillation is present on such signals and has the amplitude expected (in turn dependent on the amplitude of $VC_{plus}$ and $VC_{minus}$). In the case of a positive result, the test is passed, otherwise not.

Let's consider a self-diagnosis of the breakdown or deterioration of the components forming the measurement device. Such a self-diagnosis comprises a series of elementary tests, which may be performed ad hoc or also during the normal functioning of the system. Such elementary tests are consistency tests which provide measuring both the absolute values of the signals $V_{plus}$ and $V_{minus}$ and the related modulation oscillations $\Delta VC_{plus}$ and $\Delta VC_{minus}$; then comparing such values with certain thresholds and diagnosing the main faults or anomalies which may be present in the measurement device of the insulation resistance on the basis of such comparisons.

With reference to the aforesaid consistency and fault recognition tests, two summary tables are here reported merely by way of non-limiting example, including the results of the consistency tests and the type of fault assumed on the measurement circuit.

| | |
|---|---|
| $VC_{minus}$ < VTHRL ≈ 0 VDC | Type of fault assumable on the measurement circuit |
| | R2 short-circuited |
| | R4 short-circuited |
| | D1 short-circuited |
| | C1 short-circuited |
| | R3 circuit open |
| | $RB_{minus}$ circuit open |
| | $U_{minus}$ broken |
| | or short-circuited to ground |
| $VC_{minus}$ > VTHR-H1 | Type of fault assumable |
| | R2 circuit open |
| $VC_{minus}$ > VTHR-H2 | Type of fault assumable |
| | D1 circuit open |
| $\Delta VC_{minus}$ < VTHRL ≈ 0 VDC | Type of fault assumable |
| | R1 circuit open |
| | $RB_{minus}$ short circuit or open circuit |
| $\Delta VC_{minus}$ ≈> VTHR-H3 | Type of fault assumable |
| | C1 circuit open |
| | R2 circuit open |
| $\Delta VC_{minus}$ < VTHR-H4 | Type of fault assumable |
| | R3 circuit open | and, similarly,

| | |
|---|---|
| $VC_{plus}$ < VTHRL ≈ 0 VDC | Type of fault assumable |
| | R6 short-circuited |
| | R8 short-circuited |
| | D2 short-circuited |
| | C2 short-circuited |
| | R7 circuit open |
| | $RB_{minus}$ circuit open |
| | $U_{minus}$ broken |
| | or short-circuited to ground |
| $VC_{plus}$ > VTHR-H1 | Type of fault assumable |
| | R6 circuit open |
| $VC_{plus}$ > VTHR-H2 | Type of fault assumable |
| | D2 circuit open |
| $\Delta VC_{plus}$ < VTHRL | Type of fault assumable |
| | R5 circuit open |
| | $RB_{plus}$ short circuit or open circuit |
| $\Delta VC_{plus}$ ≈> VTHR-H3 | Type of fault assumable |
| | C2 circuit open |
| | R6 circuit open |
| $\Delta VC plus$ < VTHR-H4 | Type of fault assumable |
| | R7 circuit open |

On the basis of what disclosed above, a method of self-diagnosis of an electronic device 1 for the diagnosis of the insulation loss of an energized electrical apparatus 2 is now described, in which device 1 is according to any one of the embodiments described above.

Such a method comprises the steps of: performing a diagnosis of the functioning of the first resistance-switch group ($RS_{minus}$, $S_{minus}$) and of the second resistance-switch group ($RS_{plus}$, $S_{plus}$) of the device on the basis of measurements of the first $VC_{minus}$ and of the second detection voltage $VC_{plus}$, performed by the device under conditions in which the first sample resistance input switch $S_{minus}$ and the second sample resistance input switch $S_{plus}$ are arranged under a plurality of conditions, respectively, belonging to the following set of conditions: open, open; closed, open; open, closed; closed, closed.

The method then provides performing a consistency test of the measurement taken by the device on the basis of the first detection voltage $VC_{minus}$ and the second detection voltage $VC_{plus}$, as measured by the device, and of the battery voltage $V_B$ (that is the difference between the positive voltage $V_{plus}$ and the negative voltage $V_{minus}$ of the battery), the value of which is available regardless of the measurements of device 1.

The method also provides checking the presence and measuring the amplitude of a first oscillation $VC_{minus}$ of the first detection voltage $VC_{minus}$ around its steady state value while the first modulation switch SW1 switches between opening and closing, and further checking the presence and measuring the amplitude of a second oscillation $\Delta VC_{plus}$ of the second detection voltage $VC_{plus}$ around its steady state value while the second modulation switch SW2 switches between opening and closing.

Finally, the method provides performing a diagnosis of the functioning of the first measurement circuit and of the second measurement circuit of the device on the basis of measurements of the first detection voltage $VC_{minus}$, the second detection voltage $VC_{plus}$, the amplitude of the first oscillation $VC_{minus}$ and the amplitude of the second oscillation $\Delta VC_{plus}$.

According to one particular embodiment of the self-diagnosis method, it comprises, prior to the step of performing a diagnosis of the functioning of the first resistance-switch group 13, the further step of performing a diagnosis of the functioning of the devices switches ($M_{minus}$, $M_{plus}$) on the basis of the first detection voltage $VC_{minus}$ and of the second detection voltage $VC_{plus}$, which are measured by the device under condition of closed device switches $M_{minus}$, $M_{plus}$.

According to an implementation option of the self-diagnosis method, the step of performing a diagnosis of the functioning of the resistance-switch groups comprises measuring the first $VC_{minus}$ and the second detection voltage $VC_{plus}$ under conditions in which the first sample resistance input switch $S_{minus}$ and the second sample resistance input switch $S_{plus}$ are arranged, respectively, under the following conditions: open, open; closed, open; open, closed; closed, closed.

According to an implementation example of the self-diagnosis method, the step of performing a diagnosis of the functioning of the resistance-switch groups 13, 14 comprises the following first, second, third and fourth tests.

The first test comprises opening the first sample resistance input switch $S_{minus}$ and the second sample resistance input switch $S_{plus}$, measuring the first $VC_{minus}$ and the second detection voltage $VC_{plus}$ after reaching a steady state condition; then comparing the absolute value of the difference between the first and second detection voltage with a first threshold THR0, and determining a positive result of the first test if such an absolute value of the difference is less than the first threshold THR0 (in fact, a high voltage value is a symptom of an unbalancing of the two insulation resistances).

In one implementing example, the first test further comprises comparing the absolute value of the difference between the first and second detection voltage with a calibration threshold THRc to determine a first or a second value for the second threshold THR1 and for a third threshold THR2 (which will be employed in the successive tests), depending on whether the absolute value of the difference is higher or lower than the calibration threshold THRc.

The second test comprises closing the first sample resistance input switch $S_{minus}$ and opening the second sample resistance input switch $S_{plus}$ after reaching a steady state condition; then measuring the first $VC_{minus}$ and the second detection voltage $VC_{plus}$, comparing the difference between the second detection voltage $VC_{plus}$ and the first detection voltage $VC_{minus}$ with the value determined (or saved) for the second threshold THR1, and determining a positive result of the second test if such a difference is greater than the second threshold THR1.

The third test comprises opening the first sample resistance input switch $S_{minus}$ and closing the second sample resistance input switch $S_{plus}$, measuring the first $VC_{minus}$ and the second detection voltage $VC_{plus}$, comparing the difference between the first detection voltage $VC_{minus}$ and the second detection voltage $VC_{plus}$ with the value determined (or saved) for the second threshold THR1, and determining a positive result of the third test if such a difference is greater than the second threshold THR1.

The fourth test comprises closing the first sample resistance input switch $S_{minus}$ and the second sample resistance input switch $S_{plus}$, measuring the first $VC_{minus}$ and the second detection voltage $VC_{plus}$, comparing the absolute value of the difference between the first and the second detection voltage with the value determined (or saved) for the third threshold THR2 and determining a positive result of the fourth test if such an absolute value of the difference is less than the third threshold THR2.

The method finally provides diagnosing a correct functioning of the resistance-switch groups if all the four tests shown above provide a positive result.

It is worth noting that the diagnosis of functioning of the resistance-switch groups may be performed in various manners. For example, according to an option alternative to the preceding one, such a diagnosis may be performed in the following manner.

The input switches of sample resistance $S_{minus}$ and $S_{plus}$ initially are open (while the switching switches SW1 and SW2 may be indifferently open or closed or in the step of switching). The voltages $VC_{minus}$ and $VC_{plus}$ are measured under such conditions.

Then, any one between $S_{minus}$ and $S_{plus}$ is closed and a check is made whether the respective insertion of the sample resistance $RS_{minus}$ or $RS_{plus}$ generates the unbalancing expected on the voltages $VC_{minus}$ and $VC_{plus}$.

In particular, by indicating the voltages measured initially as $VC_{minus-1}$ and $VC_{plus-1}$, the voltages measured after the closing of one between $S_{minus}$ and $S_{plus}$ as $VC_{minus-2}$ and $VC_{plus-2}$ and two conveniently predefined thresholds with $THRVC_{minus}$ and $THRVC_{plus}$ so that the test is successfully passed, if $S_{minus}$ is closed, it is necessary that:

$$VC_{minus-2} < VC_{minus-1} - THRVC_{minus}$$

$$VC_{plus-2} > VC_{plus-1} + THRVC_{plus}$$

and if instead $S_{plus}$ is closed:

$$VC_{minus-2} > VC_{minus-1} + THRVC_{minus}$$

$$VC_{plus-2} < VC_{plus-1} - THRVC_{plus}$$

According to an implementation option of the self-diagnosis method, the step of performing a consistency test of the measurement taken by the device comprises: calculating the sum of the first detection voltage $VC_{minus}$ and of the second detection voltage $VC_{plus}$; storing the difference between the positive $V_{plus}$ and negative $V_{minus}$ voltage of the battery, on the basis of the battery voltage $V_B$ (which is precisely the difference between the positive voltage and the negative voltage of the battery) which is known independently on the measurements of the device (for example, known to a battery management system BMS of higher level); then calculating a comparison value by weighing the battery voltage with a factor (A) dependent on the electrical parameters of the device; finally, determining a positive result of the consistency test if the aforesaid sum of the first detection voltage $VC_{minus}$ and the second detection voltage $VC_{plus}$ differs from the aforesaid comparison value by less than a predefined amount.

In a particular implementing option, factor A is given by the following expression:

$$A = \left( \frac{2R_1 + 2R_3 + R_2}{R_2(2R_1 + R_3)} * \frac{2R_1R_3 + R_3^2 + 2RB(R_1 + R_3)}{2(R_1 + R_3)} + \frac{2R_1 + R_3}{2(R_1 + R_3)} \right)$$

According to one implementation option of the self-diagnosis method, the step of checking the presence and measuring the amplitude of a first and a second oscillation comprises: switching the first modulation switch SW1 between opening and closing, by the first driving signal; then measuring the first detection voltage maximum value $VC_{minus\text{-}MAX}$ and the first detection voltage minimum value $VC_{minus\text{-}MIN}$ and calculating the difference between such maximum value and minimum value of first detection voltage to determine the first oscillation amplitude $\Delta VC_{minus}$.

Similarly, it is provided to switch the second modulation switch SW2 between opening and closing, by the second driving signal; then measuring the second detection voltage maximum value $VC_{plus\text{-}MAX}$ and the second detection voltage minimum value $VC_{plus\text{-}MIN}$ and calculating the difference between such maximum value and minimum value of second detection voltage to determine the second oscillation amplitude $\Delta VC_{plus}$.

Then, it is checked whether the first oscillation amplitude $\Delta VC_{minus}$ remains within a predefined range of acceptable values, which is dependent on the first detection voltage $VC_{minus}$, and whether the second oscillation amplitude $\Delta VC_{plus}$ is kept within a predefined range of acceptable values, which is dependent on the second detection voltage $VC_{plus}$.

According to one implementation option of the self-diagnosis method, the step of performing a diagnosis of the functioning of the first (15) and second measurement circuit (16) comprises: identifying a first group of possible faults of the first measurement circuit 15 if the first detection voltage $VC_{minus}$ is lower than a low threshold (VTHRL); identifying a second group of possible faults of the first measurement circuit 15 if the first detection voltage $VC_{minus}$ is higher than a first high threshold VTHR-H1; identifying a third group of possible faults of the first measurement circuit 15 if the amplitude of the first oscillation $\Delta VC_{minus}$ is lower than a low threshold VTHRL; identifying a fourth group of possible faults of the first measurement circuit 15 if the amplitude of the first oscillation $\Delta VC_{minus}$ is higher than a second high threshold VTHR-H2; identifying a first group of possible faults of the second measurement circuit 16 if the second detection voltage $VC_{plus}$ is lower than a low threshold VTHRL; identifying a second group of possible faults of the second measurement circuit 16 if the second detection voltage $VC_{plus}$ is higher than a third high threshold VTHR-H3; identifying a third group of possible faults of the second measurement circuit 16 if the amplitude of the second oscillation $\Delta VC_{plus}$ is lower than a low threshold VTHRL; identifying a fourth group of possible faults of the second measurement circuit 16 if the amplitude of the second oscillation $\Delta VC_{plus}$ is higher than a fourth high threshold VTHR-H4; finally, determining a correct functioning of the first (15) and the second measurement circuit (16) if no fault is identified as a result of the preceding steps of identifying.

For an exemplification of the aforesaid groups of faults which may be detected and identified by the above-described method, refer to the summary tables of the test results indicated above in the present description.

As may be noted, the object of the present invention is fully achieved by the above-described measurement device, measurement system, measurement method and self-diagnosis method, in light of the features thereof.

Indeed, due to the "dynamic" measurement technique employed, that is a "switching" technique, the measurement device is capable of measuring the insulation resistances in an accurate and adaptable manner within a broad range of insulation resistances and measurement voltages. In particular, the proportionality factory between the voltages detected ($VC_{minus}$ and $VC_{plus}$) and the battery voltages ($V_{minus}$ and $V_{plus}$) can be dynamically varied and adjusted according to the voltages measured, as noted above.

Moreover, due to the structure thereof, the device according to the invention allows to perform effective and simultaneously simple self-diagnosis procedures (shown above in detail), which are adapted to check the correct functioning of the device itself and to accurately identify a possible fault among a plurality of several possible faults which can be detected.

Overall, the device, system and methods described have various innovative aspects (as already shown in detail) which achieve the object of improving the accuracy of the measurement and the diagnosis while significantly decreasing the costs of the device with respect to the solutions commonly used in the prior art; and moreover, they achieve the object of making the measurement device easily self-diagnosable to check the correct functioning and integrity thereof over time, without the need to turn to redundant and costly measurement circuits.

Those skilled in the art may make several changes and adaptations to the above-described embodiments of the measurement device, measurement system, measurement method and self-diagnosis method, and may replace elements with others which are functionally equivalent in order to meet contingent needs, without departing from the scope of the following claims.

All of the features described above as belonging to a possible embodiment may be implemented irrespective of the other embodiments described. Furthermore, it is also worth noting that the term "comprising" does not exclude other elements or steps, the term "one" does not exclude a plurality. The drawings are not to scale since we favor the requirement of conveniently noting the various parts for increased illustrative clarity.

The invention claimed is:

1. The electronic device for the diagnosis of insulation loss, with respect to a ground of an energized electrical apparatus having a negative terminal and a positive terminal, through the measurement of a negative terminal insulation resistance ($RI_{minus}$) present between said negative terminal and said ground, and a positive terminal insulation resistance ($RI_{plus}$) present between said positive terminal and said ground, the device including:

a first device terminal and a second device terminal, suitable to be connected, respectively, to the negative and positive terminals of the energized electrical apparatus;

a first resistance-switch group, comprising a first sample resistance ($RS_{minus}$) adapted to be connected or disconnected in a controlled manner between the first device terminal and the ground by a first sample resistance insertion switch ($S_{minus}$);

a first measurement circuit, arranged between the first device terminal and the ground, in parallel to the first resistance-switch group;

a second resistance-switch group, comprising a second sample resistance ($RS_{plus}$) adapted to be connected or disconnected in a controlled manner between the second device terminal and the ground by a second sample resistance insertion switch ($S_{plus}$);

a second measurement circuit, arranged between the second device terminal and the ground, in parallel to the second resistance-switch group;

wherein the first measurement circuit comprises:

a first detection circuit, comprising at least a first resistor (R2) and a first capacitor (C1) arranged mutually in parallel, so that at the ends of the first capacitor (C1), after the first device terminal is connected to the energized electrical apparatus and reaches a first steady state, there is a first detection voltage ($VC_{minus}$) depending on the negative voltage ($V_{minus}$) of the energized electrical apparatus; the first detection circuit further comprising a first voltage meter ($U_{minus}$);

a first charge modulation circuit, arranged in parallel to the first detection circuit, and comprising a first modulation resistance (R1) and a first modulation switch (SW1), arranged in series with the first modulation resistance (R1) and adapted to be controlled by a first driving signal ($V_{SW-minus}$), so that, when the first device terminal is connected to the energized electrical apparatus, the first capacitor (C1) is partially discharged and recharged, respectively, during each closing and opening period of the first modulation switch (SW1), so that the first detection voltage ($VC_{minus}$) oscillates between a first detection voltage maximum value ($VC_{minus-MAX}$) and a first detection voltage minimum value ($VC_{minus-MIN}$), around a first detection voltage intermediate value ($VC_{minus}$) representative of the negative voltage ($V_{minus}$) of the energized electrical apparatus;

a first partition resistor ($RB_{minus}$) connected between the first device terminal and the first detection circuit, so that the first partition resistor ($RB_{minus}$) and the first detection circuit are arranged mutually in series;

and wherein the second measurement circuit comprises:

a second detection circuit, comprising at least a second resistor (R6) and a second capacitor (C2) arranged mutually in parallel, so that at the ends of the second capacitor (C2), after the second device terminal is connected to the energized electrical apparatus and reach a second steady state, there is a second detection voltage ($VC_{plus}$) depending on the positive voltage ($V_{plus}$) of the energized electrical apparatus; the second detection circuit further comprising a second voltage meter ($U_{plus}$);

a second charge modulation circuit, arranged in parallel to the second detection circuit, and comprising a second modulation resistance (R5) and a second modulation switch (SW2), arranged in series with the second modulation resistance (R5) and adapted to be controlled by a second driving signal ($V_{SW-plus}$), so that, when the second device terminal is connected to the energized electrical apparatus, the second capacitor (C2) is partially discharged and recharged, respectively, during each closing and opening period of the second modulation switch (SW2), so that the second detection voltage ($VC_{plus}$) oscillates between a second detection voltage maximum value ($VC_{plus-MAX}$) and a second detection voltage minimum value ($VC_{plus-MIN}$), around a second detection voltage intermediate value ($VC_{plus}$) representative of the positive voltage ($V_{plus}$) of the energized electrical apparatus;

a second partition resistor ($RB_{plus}$) connected between the second device terminal and the second detection circuit, so that the second partition resistor ($RB_{plus}$) and the second detection circuit are arranged mutually in series;

wherein said first voltage meter ($U_{minus}$) is configured to provide the first detection voltage ($VC_{minus}$) under both opening and closing conditions of the first resistance-switch group switch ($S_{minus}$), in which conditions the first sample resistance ($RS_{minus}$) is connected and disconnected, respectively;

and wherein said second voltage meter ($U_{plus}$) is configured to provide the second detection voltage ($VC_{plus}$) under both opening and closing conditions of the second resistance-switch group switch ($S_{plus}$) in which conditions the second sample resistance ($RS_{plus}$) is connected and disconnected, respectively.

2. The device according to claim 1, comprising:

a first device switch ($M_{minus}$), adapted to connect or disconnect in a controlled manner the first terminal of the device to/from the negative terminal of the energized electrical apparatus;

a second device switch ($M_{plus}$), adapted to connect or disconnect in a controlled manner the second terminal of the device to/from the positive terminal of the energized electrical apparatus.

3. The device according to claim 1, wherein:

the first detection circuit further comprises a third resistor (R3) connected between the parallel of the first resistor (R2) and first capacitor (C1) and the ground;

the second detection circuit further comprises a fourth resistor (R7) connected between the parallel of the second resistor (R6) and second capacitor (C2) and the ground.

4. The device according to claim 1, wherein the first measurement circuit and the second measurement circuit have an identical circuit structure and have electrical parameters of corresponding resistors and capacitors respectively identical.

5. The device according to claim 1, wherein:

each of said first device switch ($M_{minus}$) and second device switch ($M_{plus}$) comprises an electromechanical switch, and wherein each of said first modulation switch (SW1) and second modulation switch (SW2) comprises a respective solid state electronic switch.

6. The device according to claim 1, wherein each of said first voltage meter ($U_{minus}$) and second voltage meter ($U_{plus}$) comprises a respective operational amplifier.

7. An electronic system for the diagnosis of the insulation loss of an energized electrical apparatus, comprising an electronic device according to claim 1, and further comprising a control device, wherein the control device is configured to:

generate and provide to the first modulation switch (SW1) said first driving signal ($V_{SW-minus}$);

generate and provide to the second modulation switch (SW2) said second driving signal ($V_{SW-plus}$);

receive the first detection voltage ($VC_{minus}$) from the first voltage meter ($U_{minus}$) and the second detection voltage ($VC_{plus}$) from the second voltage meter ($U_{plus}$);

determine a first value of first detection voltage ($VC1_{minus}$), under condition of disconnection of the first sample resistance ($RS_{minus}$), and determine a second value of first detection voltage ($VC2_{minus}$), under condition of connection of the first sample resistance ($RS_{minus}$);

determine a first value of second detection voltage ($VC1_{plus}$), under condition of disconnection of the second sample resistance ($RS_{plus}$), and determine a second value of second detection voltage ($VC2_{plus}$), under condition of connection of the second sample resistance ($RS_{plus}$);

calculate the negative terminal insulation resistance ($RI_{minus}$) and the positive terminal insulation resistance ($RI_{plus}$) of the energized electrical apparatus, on the basis of said first value of first detection voltage ($VC1_{minus}$) and second value of first detection voltage ($VC2_{minus}$) and/or said first value of second detection voltage ($VC1_{plus}$) and second value of second detection voltage ($VC2_{plus}$).

8. The system according to claim 7, further configured to:

determine the first value of first detection voltage ($VC1_{minus}$), on the basis of said first detection voltage maximum value ($VC1_{minus-MAX}$) and first detection voltage minimum value ($VC1_{minus-MIN}$), in conditions of disconnection of the first sample resistance ($RS_{minus}$), and determine the second value of first detection voltage ($VC2_{minus}$), on the basis of said first detection voltage maximum value ($VC2_{minus-MAX}$) and first detection voltage minimum value ($V2C_{minus-MIN}$), in condition of connection of the first sample resistance ($RS_{minus}$);

determine the first value of second detection voltage ($VC1_{plus}$), on the basis of said second detection voltage maximum value ($VC1_{plus-MAX}$) and second detection voltage minimum value ($VC1_{plus-MIN}$), in conditions of disconnection of the second sample resistance ($RS_{plus}$), and determine the second value of second detection voltage ($VC2_{plus}$), on the basis of said second detection voltage maximum value ($VC2_{plus-MAX}$) and second detection voltage minimum value ($V2C_{plus-MIN}$), in conditions of connection of the second sample resistance ($RS_{plus}$).

9. The system according to claim 7, wherein:

said first driving signal ($V_{SW-minus}$) is a pulse signal having a first frequency, wherein the presence and absence of the pulse control the closing and opening, or the opening and closing, of the first modulation switch (SW1), and wherein the pulse duration with respect to the period associated with the first frequency defines a first close-open duty-cycle (DC1);

said second driving signal ($V_{SW-plus}$) is a pulse signal having a second frequency, wherein the presence and absence of the pulse control the closing and opening, or the opening and closing, of the second modulation switch (SW2), and wherein the pulse duration with respect to the period associated with the second frequency defines a second close-open duty-cycle (DC2).

10. The system according to claim 9, wherein the control device is further configured to dynamically adjust, during the measurement, one or any combination of the following parameters: first frequency of the first driving signal ($V_{SW-minus}$); second frequency of the second driving signal ($V_{SW-plus}$); first close-open duty-cycle (DC1); second close-open duty-cycle (DC2).

11. The system according to claim 9, wherein:

the first and the second driving signal ($V_{SW-minus}$, $V_{SW-plus}$) are periodic signals of Pulse Width Modulation (PWM) type;

the first and the second driving frequency are equal to each other;

the first closing-opening duty-cycle (DC1) and the second close-open duty-cycle (DC2) are equal to each other;

the first driving signal ($V_{SW-minus}$) and the second driving signal ($V_{SW-plus}$) are equal or complementary to each other.

12. Method A method for measuring a negative terminal insulation resistance ($RI_{minus}$), present between a negative terminal and the ground of an energized electrical apparatus, and a positive terminal insulation resistance ($RI_{plus}$), present between a positive terminal and the ground of the energized electrical apparatus, the method comprising the steps of:

connecting a first measurement circuit between said negative terminal and ground to detect a first value ($VC1_{minus}$) of a first detection voltage ($VC_{minus}$), depending on the negative voltage ($V_{minus}$) of the energized electrical apparatus;

connecting a second measurement circuit between said positive terminal and ground to detect a first value ($VC_{plus}$) of a second detection voltage ($VC_{plus}$), depending on the positive voltage ($V_{plus}$) of the energized electrical apparatus;

alternatively, connecting a first sample resistance ($RS_{minus}$) in parallel to the first measurement circuit between said negative terminal and ground, or connecting a second sample resistance ($RS_{plus}$) in parallel to the second measurement circuit between said positive terminal and ground;

under said connection condition of connection of one of the first sample resistance ($RS_{minus}$) and the second sample resistance ($RS_{plus}$), detecting a second value ($VC2_{minus}$) of the first detection voltage ($VC_{minus}$), and detecting a second value ($VC2_{plus}$) of the second detection voltage ($VC_{plus}$);

calculating the negative terminal insulation resistance ($RI_{minus}$) and the positive terminal insulation resistance ($RI_{plus}$) of the energized electrical apparatus, on the basis of said first value of first detection voltage ($VC1_{minus}$), second value of first detection voltage ($VC2_{minus}$), first value of second detection voltage ($VC1_{plus}$) and second value of second detection voltage ($VC2_{plus}$);

wherein said step of detecting a first value of first detection voltage ($VC1_{minus}$) comprises modulating the first detection voltage ($VC_{minus}$) by use of a modulation signal, detecting the modulated first detection voltage ($VC_{minus}$), and determining the first value of first detection voltage ($VC1_{minus}$) on the basis of the modulated first detection voltage ($VC_{minus}$);

wherein said step of detecting a first value of second detection voltage ($VC1_{plus}$) comprises modulating the second detection voltage ($VC_{plus}$) by of a modulation signal, detecting the modulated second detection voltage ($VC_{plus}$), and determining the first value of second detection voltage ($VC_{plus}$) on the basis of the modulated second detection voltage ($VC_{plus}$);

wherein said step of detecting a second value of first detection voltage ($VC2_{minus}$) comprises: modulating again the first detection voltage ($VC_{minus}$) by of the modulation signal, while said first sample resistance ($RS_{minus}$) or second sample resistance ($RS_{plus}$) is connected; detecting again the modulated first detection voltage ($VC_{minus}$); determining the second value of first detection voltage ($VC2_{minus}$) on the basis of the modulated first detection voltage ($VC_{minus}$), detected while said first sample resistance ($RS_{minus}$) or second sample resistance ($RS_{plus}$) is connected;

and wherein said step of detecting a second value of second detection voltage ($VC2_{plus}$) comprises: modulating again the second detection voltage ($VC_{plus}$) by of the modulation signal, while said first sample resistance ($RS_{minus}$) or second sample resistance ($RS_{plus}$) is connected; detecting again the modulated second detection voltage ($VC_{plus}$); determining the second value of second detection voltage ($VC2_{plus}$) on the basis of the modulated second detection voltage ($VC_{plus}$), while said first sample resistance ($RS_{minus}$) or second sample resistance ($RS_{plus}$) is connected.

13. The method according to claim 12, including, prior to the step of connecting the first or second sample resistance, the further step of comparing the first value of first detection voltage ($VC1_{minus}$) and the first value of second detection voltage ($VC_{plus}$);

and wherein said step of connecting a first sample resistance ($RS_{minus}$) or a second sample resistance ($RS_{plus}$) comprises:

connecting the first sample resistance ($RS_{minus}$), keeping the second sample resistance ($RS_{plus}$) disconnected, if the first detection voltage ($VC_{minus}$) is greater than the second detection voltage ($VC_{plus}$);

connecting the second sample resistance ($RS_{plus}$), keeping the first sample resistance ($RS_{minus}$) disconnected, if the first detection voltage ($VC_{minus}$) is less than the second detection voltage ($VC_{plus}$).

14. The method according to claim 12, wherein:

the step of modulating the first detection voltage ($VC_{minus}$) comprises modulating the first detection voltage ($VC_{minus}$) so that it oscillates between a first detection voltage maximum value ($VC1_{minus-MAX}$) and a first detection voltage minimum value ($VC1_{minus-MIN}$);

the step of modulating again the first detection voltage ($VC_{minus}$) comprises modulating again the first detection voltage ($VC_{minus}$) so that it oscillates between a new first detection voltage maximum value ($VC2_{minus-MAX}$) and a new first detection voltage minimum value ($VC2_{minus-MIN}$);

the step of modulating the second detection voltage ($VC_{plus}$) comprises modulating the second detection voltage ($VC_{plus}$) so that it oscillates between a of second detection voltage maximum value ($VC1_{plus-MAX}$) and a of second detection voltage minimum value ($VC1_{plus-MIN}$);

the step of modulating again the second detection voltage ($VC_{plus}$) comprises modulating the second detection voltage ($VC_{plus}$) so that it oscillates between a new second detection voltage maximum value ($VC2_{plus-MAX}$) and a new second detection voltage minimum value ($VC2_{plus}$-MIN).

15. The method according to claim 14, wherein:

the step of detecting the first detection voltage comprises measuring said first detection voltage maximum value ($VC1_{minus-MAX}$) and first detection voltage minimum value ($VC1_{minus-MIN}$); and the step of determining a first value of first detection voltage comprises determining the first value of first detection voltage ($VC1_{minus}$) on the basis of said first detection voltage maximum value ($VC1_{minus-MAX}$) and first detection voltage minimum value ($VC1_{minus-MIN}$);

the step of detecting again the first detection voltage comprises measuring again the first detection voltage maximum value ($VC2_{minus-MAX}$) and the first detection voltage minimum value ($VC2_{minus-MIN}$), while the first sample resistance ($RS_{minus}$) or the second sample resistance ($RS_{plus}$) is connected; and the step of determining a second value of first detection voltage comprises determining the second value of first detection voltage ($VC2_{minus}$) on the basis of said first detection voltage maximum value ($VC2_{minus-MAX}$) and first detection voltage minimum value ($VC2_{minus-MIN}$), detected while the first sample resistance ($RS_{minus}$) or the second sample resistance ($RS_{plus}$) is connected;

the step of detecting the second detection voltage comprises measuring said second detection voltage maximum value ($VC1_{plus-MAX}$) and second detection voltage minimum value ($VC1_{plus-MIN}$); and the step of determining a first value of second detection voltage comprises determining the first value of second detection voltage ($VC_{plus}$) on the basis of said second detection voltage maximum value ($VC1_{plus-MAX}$) and second detection voltage minimum value ($VC1_{plus-MIN}$);

the step of detecting again the second detection voltage comprises measuring again the second detection voltage maximum value ($VC2_{plus}$-MAX) and the second detection voltage minimum value ($VC2_{plus}$-MIN), while the first sample resistance ($RS_{minus}$) or the second sample resistance ($RS_{plus}$) is connected; and the step of determining a second value of second detection voltage comprises determining the second value of second detection voltage ($VC2_{plus}$) on the basis of said second detection voltage maximum value ($VC2_{plus-MAX}$) and second detection voltage minimum value ($VC2_{plus-MIN}$), detected while the first sample resistance ($RS_{minus}$) or the second sample resistance ($RS_{plus}$) is connected.

16. The method for diagnosing an insulation loss of an energized electrical apparatus, comprising:

measuring a negative terminal insulation resistance ($RI_{minus}$), present between a negative terminal and the ground of an energized electrical apparatus, and a positive terminal insulation resistance ($RI_{plus}$), present between a positive terminal and the ground of the energized electrical apparatus;

diagnosing the insulation loss of the energized electrical apparatus on the basis of the negative terminal insulation resistance ($RI_{minus}$) measured and of the positive terminal insulation resistance ($RI_{plus}$) measured, wherein said measuring step is performed by a method according to claim 12.

17. The method of self-diagnosis of an electronic device for diagnosing the insulation loss of an energized electrical apparatus, the device being according to claim 1, the method comprising the steps of:

performing a diagnosis of the functioning of the first resistance-switch group ($RS_{minus}$, $S_{minus}$) and of the second resistance-switch group ($RS_{plus}$, $S_{plus}$) of the device, on the basis of measurements of the first ($VC_{minus}$) and of the second detection voltage ($VC_{plus}$), carried out by the device under conditions in which the first sample resistance input switch ($S_{minus}$) and the second sample resistance input switch ($S_{plus}$) are in a plurality of conditions, respectively, belonging to the following set of conditions: open, open; closed, open; open, closed; closed, closed;

performing a consistency test of the measurement made by the device on the basis of the first detection voltage ($VC_{minus}$) and the second detection voltage ($VC_{plus}$), as measured by the device, and of the battery voltage (VB), the value of which is available regardless of the measurements of the device;

checking the presence and measuring the amplitude of a first oscillation ($\Delta VC_{minus}$) of the first detection voltage ($VC_{minus}$) around its steady state value, while the first modulation switch (SW1) switches between opening and closing, and further checking the presence and measuring the amplitude of a second oscillation ($\Delta VC_{plus}$) of the second detection voltage ($VC_{plus}$) around its steady state value, while the second modulation switch (SW2) switches between opening and closing;

performing a diagnosis of the functioning of the first measurement circuit and of the second measurement circuit of the device, on the basis of measurements of the first detection voltage ($VC_{minus}$), the second detection voltage ($VC_{plus}$), the amplitude of the first oscillation ($\Delta VC_{minus}$) and the amplitude of the second oscillation ($\Delta VC_{plus}$).

18. A self-diagnosis method according to claim 17, wherein the method comprises, before the step of performing a diagnosis of the functioning of the first resistance-switch group, the further step of:

performing a diagnosis of the functioning of the device switches ($M_{minus}$, $M_{plus}$), on the basis of the first detection voltage ($VC_{minus}$) and of the second detection voltage ($VC_{plus}$), measured by the device in condition of closed device switches ($M_{minus}$, $M_{plus}$).

19. The self-diagnosis method according to claim 17, wherein the step of performing a diagnosis of the functioning of the resistance-switch groups comprises measuring the first ($VC_{minus}$) and the second detection voltage ($VC_{plus}$), under conditions in which the first sample resistance input switch ($S_{minus}$) and the second sample resistance input switch ($S_{plus}$) are respectively set in the following conditions: open, open; closed, open; open, closed; closed, closed.

20. The self-diagnosis method according to claim 19, wherein the step of performing a diagnosis of the functioning of the resistance-switch groups comprises:

a first test comprising opening the first sample resistance input switch ($S_{minus}$) and the second sample resistance input switch ($S_{plus}$), measuring the first ($VC_{minus}$) and the second detection voltage ($VC_{plus}$), comparing the absolute value of the difference between said first and second detection voltage with a first threshold (THR0), and determining a positive result of the first test if said absolute value of the difference is less than the first threshold (THR0);

a second test comprising closing the first sample resistance input switch ($S_{minus}$) and opening the second sample resistance input switch ($S_{plus}$), measuring the first ($VC_{minus}$) and the second detection voltage ($VC_{plus}$), comparing the difference between the second detection voltage ($VC_{plus}$) and the first detection voltage ($VC_{minus}$) with a second threshold (THR1), and determining a positive result of the second test if said difference is greater than the second threshold (THR1);

a third test comprising opening the first sample resistance input switch ($S_{minus}$) and closing the second sample resistance input switch ($S_{plus}$), measuring the first ($VC_{minus}$) and the second detection voltage ($VC_{plus}$), comparing the difference between the first detection voltage ($VC_{minus}$) and the second detection voltage ($VC_{plus}$) with said second threshold (THR1), and determining a positive result of the third test if said difference is greater than the second threshold (THR1);

a fourth test comprising closing the first sample resistance input switch ($S_{minus}$) and the second sample resistance input switch ($S_{plus}$), measuring the first ($VC_{minus}$) and the second detection voltage ($VC_{plus}$), comparing the absolute value of the difference between said first and second detection voltage with a third threshold (THR2), and determining a positive result of the fourth test if said absolute value of the difference is less than the third threshold (THR2);

diagnosing a correct functioning of the resistance-switch groups if said first, second, third and fourth tests all provide a positive result.

21. The self-diagnosis method according to claim 20, wherein said first test further comprises comparing the absolute value of the difference between said first and second detection voltage with a calibration threshold (THRc) to determine a first or a second value for the second threshold (THR1) and a first or a second value for the third threshold (THR2), depending on whether said absolute value of the difference is higher or lower than the calibration threshold (THRc).

22. The self-diagnosis method according to claim 17, wherein the step of performing a consistency test of the measurement made by the device comprises:

calculating the sum of the first detection voltage ($VC_{minus}$) and of the second detection voltage ($VC_{plus}$);

storing the difference between the positive ($V_{plus}$) and negative ($V_{minus}$) voltage of the battery, on the basis of the battery voltage (VB) that known is irrespective of the measurements of the device;

calculating a comparison value, by weighing said difference between the battery voltages with a factor (A) dependent on the electrical parameters of the device;

determining a positive result of the consistency test if said sum of the first detection voltage ($VC_{minus}$) and the second detection voltage ($VC_{plus}$) differs from said comparison value by less than a predefined amount.

23. The self-diagnosis method according to claim 17, wherein the step of checking the presence and measuring the amplitude of a first and of a second oscillation comprises:

switching the first modulation switch (SW1) between opening and closing, by the first driving signal;

measuring the first detection voltage maximum value ($VC_{minus-MAX}$) and the first detection voltage minimum value ($VC_{minus-MIN}$), and calculating the difference between said maximum value and minimum value of first detection voltage to determine the first oscillation amplitude ($\Delta VC_{minus}$);

switching the second modulation switch (SW2) between opening and closing, by the second driving signal;

measuring the of second detection voltage maximum value ($VC_{plus-MAX}$) and the second detection voltage minimum value ($VC_{plus-MIN}$), and calculating the difference between said maximum value and minimum value of second detection voltage to determine the second oscillation amplitude ($\Delta VC_{plus}$);

checking that the first oscillation amplitude ($\Delta VC_{minus}$) remains within a predefined range of acceptable values, dependent on the first detection voltage ($VC_{minus}$);

checking that the second oscillation amplitude ($\Delta VC_{plus}$) remains within a predefined range of acceptable values, dependent on the second detection voltage ($VC_{plus}$).

24. The self-diagnosis method according to claim 17, wherein the step of performing a diagnosis of the functioning of the first and second measurement circuit comprises:

identifying a first group of possible faults of the first measurement circuit if the first detection voltage ($VC_{minus}$) is lower than a low threshold (VTHRL);

identifying a second group of possible faults of the first measurement circuit if the first detection voltage ($VC_{minus}$) is higher than a first high threshold (VTHR-H1);

identifying a third group of possible faults of the first measurement circuit if the amplitude of the first oscillation ($\Delta VC_{minus}$) is lower than a low threshold (VTHRL);

identifying a fourth group of possible faults of the first measurement circuit if the amplitude of the first oscillation ($\Delta VC_{minus}$) is higher than a second high threshold (VTHR-H2);

identifying a first group of possible faults of the second measurement circuit if the second detection voltage ($VC_{plus}$) is lower than a low threshold (VTHRL);

identifying a second group of possible faults of the second measurement circuit if the second detection voltage ($VC_{plus}$) is higher than a third high threshold (VTHR-H3);

identifying a third group of possible faults of the second measurement circuit if the amplitude of the second oscillation ($\Delta VC_{plus}$) is lower than a low threshold (VTHRL);

identifying a fourth group of possible faults of the second measurement circuit if the amplitude of the second oscillation ($\Delta VC_{plus}$) is higher than a fourth high threshold (VTHR-H4);

determining a correct functioning of the first and the second measurement circuit if, as a result of the preceding steps of identifying, no fault is identified.

* * * * *

UNITED STATES PATENT AND TRADEMARK OFFICE
CERTIFICATE OF CORRECTION

PATENT NO.       : 10,175,288 B2
APPLICATION NO.  : 15/378922
DATED            : January 8, 2019
INVENTOR(S)      : Danilo Pritelli et al.

Page 1 of 1

It is certified that error appears in the above-identified patent and that said Letters Patent is hereby corrected as shown below:

In the Claims

Column 30, Line 8 (Claim 12) delete "Method A method" and insert therefor --A method--.

Column 30, Line 21 (Claim 12) delete "(VC_plus) of a second" and insert therefor --(VC1_plus) of a second--.

Column 30, Line 56 (Claim 12) delete "(VC_plus)" and insert therefor --(VC1_plus)--.

Column 32, Line 17 (Claim 15) delete "(VC_plus)" and insert therefor --(VC1_plus)--.

Column 32, Line 22 (Claim 15) delete "(VC2_plus-MAX)" and insert therefor --(VC2_plus-_MAX)--.

Column 32, Line 23 (Claim 15) delete "(VC2_plus-MIN)" and insert therefor --(VC2_plus-_MIN)--.

Column 34, Line 29 (Claim 22) delete "(VB)" and insert therefor --(V_B)--.

Signed and Sealed this
Eighteenth Day of June, 2019

Andrei Iancu
*Director of the United States Patent and Trademark Office*